(12) United States Patent
Zhang et al.

(10) Patent No.: US 7,941,206 B2
(45) Date of Patent: *May 10, 2011

(54) AUTOMATIC ORIENTATION DETERMINATION FOR ECG MEASUREMENTS USING MULTIPLE ELECTRODES

(75) Inventors: Yi Zhang, Plymouth, MN (US); Marina Brockway, Shoreview, MN (US); Carlos Alberto Ricci, Apple Valley, MN (US); Ronald W. Heil, Roseville, MN (US); Douglas R. Daum, Woodbury, MN (US); Robert J. Sweeney, Woodbury, MN (US); Aaron R. McCabe, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/694,833

(22) Filed: Jan. 27, 2010

(65) Prior Publication Data

US 2010/0198283 A1    Aug. 5, 2010

Related U.S. Application Data

(62) Division of application No. 10/876,008, filed on Jun. 24, 2004, now Pat. No. 7,706,866.

(51) Int. Cl.
*A61B 5/04* (2006.01)
(52) U.S. Cl. ........................................ 600/512; 600/513
(58) Field of Classification Search .................. 600/509, 600/511–513
See application file for complete search history.

(56) References Cited

U.S. PATENT DOCUMENTS

| 3,920,005 A | 11/1975 | Gombrich et al. |
| 4,388,927 A | 6/1983 | Schober |
| 4,550,221 A | 10/1985 | Mabusth |

(Continued)

FOREIGN PATENT DOCUMENTS

EP    0468720    1/1992

(Continued)

OTHER PUBLICATIONS

Acar et al., "SVD-based on-line exercise ECG signal orthogonalization", IEEE Transactions on Biomedical Engineering, vol. 46, No. 3, Mar. 1999. (abstract only).

(Continued)

*Primary Examiner* — Carl H Layno
*Assistant Examiner* — Luther G Behringer
(74) *Attorney, Agent, or Firm* — Hollingsworth & Funk, LLC

(57) ABSTRACT

Cardiac monitoring and/or stimulation methods and systems provide monitoring, defibrillation and/or pacing therapies. A signal processor receives a plurality of composite signals associated with a plurality of sources, separates a signal using a source separation algorithm, and identifies a cardiac signal using a selected vector. The signal processor may iteratively separate signals from the plurality of composite signals until the cardiac signal is identified. The selected vector may be updated if desired or necessary. A method of signal separation involves detecting a plurality of composite signals at a plurality of locations, separating a signal using source separation, and selecting a vector that provides a cardiac signal. The separation may include a principal component analysis and/or an independent component analysis. Vectors may be selected and updated based on changes of position and/or orientation of implanted components and changes in patient parameters such as patient condition, cardiac signal-to-noise ratio, and disease progression.

20 Claims, 12 Drawing Sheets

U.S. PATENT DOCUMENTS

| | | |
|---|---|---|
| 4,562,841 A | 1/1986 | Brockway et al. |
| 4,686,332 A | 8/1987 | Greanias et al. |
| 4,878,497 A | 11/1989 | Callaghan et al. |
| 4,928,688 A | 5/1990 | Mower |
| 4,953,551 A | 9/1990 | Mehra et al. |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |
| 5,222,493 A | 6/1993 | Sholder |
| 5,230,337 A | 7/1993 | Dahl et al. |
| 5,231,990 A | 8/1993 | Gauglitz |
| 5,261,400 A | 11/1993 | Bardy |
| 5,271,411 A | 12/1993 | Ripley et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,324,310 A | 6/1994 | Greeninger et al. |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,350,410 A | 9/1994 | Kleks et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,533 A | 5/1995 | Dubreuil |
| 5,411,539 A | 5/1995 | Neisz |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,468,254 A | 11/1995 | Hahn et al. |
| 5,520,191 A | 5/1996 | Karlsson et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,603,732 A | 2/1997 | Dahl et al. |
| 5,605,158 A | 2/1997 | Snell |
| 5,620,466 A | 4/1997 | Haefner et al. |
| 5,626,620 A | 5/1997 | Kieval et al. |
| 5,634,938 A | 6/1997 | Swanson et al. |
| 5,641,326 A | 6/1997 | Adams |
| 5,650,759 A | 7/1997 | Hittman et al. |
| 5,662,688 A | 9/1997 | Haefner et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,959 A | 12/1997 | Poore |
| 5,704,365 A | 1/1998 | Albrecht et al. |
| 5,724,984 A | 3/1998 | Arnold et al. |
| 5,779,645 A | 7/1998 | Olson et al. |
| 5,827,326 A | 10/1998 | Kroll et al. |
| 5,836,987 A | 11/1998 | Baumann et al. |
| 5,844,506 A | 12/1998 | Binstead |
| 5,855,593 A | 1/1999 | Olson et al. |
| 5,861,013 A | 1/1999 | Peck et al. |
| 5,871,512 A | 2/1999 | Hemming et al. |
| 5,873,898 A | 2/1999 | Hemming et al. |
| 5,895,414 A | 4/1999 | Sanchez-Zambrano |
| 5,916,243 A | 6/1999 | KenKnight et al. |
| 5,957,956 A | 9/1999 | Kroll et al. |
| 5,983,138 A | 11/1999 | Kramer |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,049,730 A | 4/2000 | Kristbjarnarson |
| 6,055,454 A | 4/2000 | Heemels |
| 6,101,416 A | 8/2000 | Sloman |
| 6,115,628 A | 9/2000 | Stadler et al. |
| 6,128,535 A | 10/2000 | Maarse |
| 6,134,473 A | 10/2000 | Hemming et al. |
| 6,141,581 A | 10/2000 | Olson et al. |
| 6,144,880 A | 11/2000 | Ding |
| 6,147,680 A | 11/2000 | Tareev |
| 6,148,230 A | 11/2000 | KenKnight |
| 6,148,234 A | 11/2000 | Struble |
| 6,163,724 A | 12/2000 | Hemming et al. |
| 6,169,921 B1 | 1/2001 | KenKnight et al. |
| 6,175,766 B1 | 1/2001 | Bornzin et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey et al. |
| 6,238,419 B1 | 5/2001 | Lindgren |
| 6,253,102 B1 | 6/2001 | Hsu et al. |
| 6,259,947 B1 | 7/2001 | Olson et al. |
| 6,266,554 B1 | 7/2001 | Hsu et al. |
| 6,270,457 B1 | 8/2001 | Bardy |
| 6,275,731 B1 | 8/2001 | Zhu et al. |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,301,503 B1 | 10/2001 | Hsu et al. |
| 6,312,378 B1 | 11/2001 | Bardy |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,673 B1 | 2/2002 | Ding et al. |
| 6,358,203 B2 | 3/2002 | Bardy |
| 6,360,127 B1 | 3/2002 | Ding et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,418,340 B1 | 7/2002 | Conley et al. |
| 6,424,234 B1 | 7/2002 | Stevenson |
| 6,424,865 B1 | 7/2002 | Ding |
| 6,434,428 B1 | 8/2002 | Sloman et al. |
| 6,438,409 B1 | 8/2002 | Malik et al. |
| 6,438,410 B2 | 8/2002 | Hsu et al. |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,466,820 B1 | 10/2002 | Juran et al. |
| 6,477,422 B1 | 11/2002 | Splett |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,564,106 B2 | 5/2003 | Guck et al. |
| 6,567,701 B2 | 5/2003 | Vonk |
| 6,597,951 B2 | 7/2003 | Kramer et al. |
| 6,607,509 B2 | 8/2003 | Bobroff et al. |
| 6,609,027 B2 | 8/2003 | Kroll et al. |
| 6,615,082 B1 | 9/2003 | Mandell |
| 6,615,083 B2 | 9/2003 | Kupper |

| | | |
|---|---|---|
| 6,618,619 B1 | 9/2003 | Florio et al. |
| 6,622,046 B2 | 9/2003 | Fraley et al. |
| 6,625,490 B1 | 9/2003 | McClure et al. |
| 6,631,290 B1 | 10/2003 | Guck et al. |
| 6,654,637 B2 | 11/2003 | Rouw et al. |
| 6,658,293 B2 | 12/2003 | Vonk |
| 6,690,967 B2 | 2/2004 | Meij |
| 6,701,170 B2 | 3/2004 | Stetson |
| 6,708,058 B2 | 3/2004 | Kim et al. |
| 6,725,085 B2 | 4/2004 | Schwartzman et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,871,096 B2 | 3/2005 | Hill |
| 6,881,192 B1 | 4/2005 | Park |
| 6,884,218 B2 | 4/2005 | Olson et al. |
| 6,885,893 B1 | 4/2005 | Lu |
| 6,888,538 B2 | 5/2005 | Ely et al. |
| 6,889,079 B2 | 5/2005 | Bocek et al. |
| 6,895,274 B2 | 5/2005 | Mower |
| 6,904,315 B2 | 6/2005 | Panken et al. |
| 6,925,324 B2 | 8/2005 | Shusterman |
| 6,925,330 B2 | 8/2005 | Kleine |
| 6,927,721 B2 | 8/2005 | Ostroff |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Bjorling et al. |
| 6,961,619 B2 | 11/2005 | Casey |
| 6,973,350 B1 | 12/2005 | Levine et al. |
| 6,975,904 B1 | 12/2005 | Sloman |
| 6,983,264 B2 | 1/2006 | Shimizu |
| 6,988,003 B2 | 1/2006 | Bardy et al. |
| 6,993,379 B1 | 1/2006 | Kroll |
| 6,993,389 B2 | 1/2006 | Ding |
| 6,999,817 B2 | 2/2006 | Park et al. |
| 7,006,869 B2 | 2/2006 | Bradley |
| 7,027,861 B2 | 4/2006 | Thompson |
| 7,027,868 B2 | 4/2006 | Rueter et al. |
| 7,039,459 B2 | 5/2006 | Bardy |
| 7,039,465 B2 | 5/2006 | Bardy |
| 7,043,299 B2 | 5/2006 | Erlinger |
| 7,047,073 B2 | 5/2006 | Hoijer et al. |
| 7,050,851 B2 | 5/2006 | Plombon et al. |
| 7,065,400 B2 | 6/2006 | Schechter |
| 7,065,407 B2 | 6/2006 | Bardy |
| 7,065,410 B2 | 6/2006 | Bardy et al. |
| 7,069,080 B2 | 6/2006 | Bardy |
| 7,076,296 B2 | 7/2006 | Rissmann et al. |
| 7,079,988 B2 | 7/2006 | Albera |
| 7,085,599 B2 | 8/2006 | Kim et al. |
| 7,090,682 B2 | 8/2006 | Sanders et al. |
| 7,092,754 B2 | 8/2006 | Bardy et al. |
| 7,096,064 B2 | 8/2006 | Deno et al. |
| 6,084,253 A1 | 9/2006 | Johnson et al. |
| 7,103,404 B2 | 9/2006 | Stadler et al. |
| 7,107,093 B2 | 9/2006 | Burnes |
| 7,110,817 B2 | 9/2006 | Yu et al. |
| 7,113,823 B2 | 9/2006 | Yonce et al. |
| 7,117,036 B2 | 10/2006 | Florio |
| 7,120,495 B2 | 10/2006 | Bardy et al. |
| 7,123,960 B2 | 10/2006 | Ding |
| 7,127,290 B2 | 10/2006 | Girouard |
| 7,129,935 B2 | 10/2006 | Mackey |
| 7,139,610 B2 | 11/2006 | Ferek-Patric |
| 7,144,586 B2 | 12/2006 | Levy et al. |
| 7,146,206 B2 | 12/2006 | Glass et al. |
| 7,146,212 B2 | 12/2006 | Bardy et al. |
| 7,149,575 B2 | 12/2006 | Ostroff et al. |
| 7,158,830 B2 | 1/2007 | Yu |
| 7,177,689 B2 | 2/2007 | Ternes et al. |
| 7,181,285 B2 | 2/2007 | Lindh |
| 7,184,825 B2 | 2/2007 | Leinsing et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al. |
| 7,225,021 B1 | 5/2007 | Park et al. |
| 7,228,173 B2 | 6/2007 | Cazares |
| 7,228,174 B2 | 6/2007 | Burnes |
| 7,236,819 B2 | 6/2007 | Brockway |
| 7,242,978 B2 | 7/2007 | Cao |
| 7,245,962 B2 | 7/2007 | Ciaccio et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,319,900 B2 | 1/2008 | Kim et al. |
| 7,359,749 B2 | 4/2008 | Quenet et al. |
| 7,457,664 B2 | 11/2008 | Zhang et al. |
| 7,558,628 B2 | 7/2009 | Yonce et al. |
| 7,697,985 B2 | 4/2010 | Kaiser et al. |
| 7,853,317 B2 | 12/2010 | Duann et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0042629 A1 | 4/2002 | Bardy et al. |
| 2002/0042634 A1 | 4/2002 | Bardy et al. |
| 2002/0082658 A1 | 6/2002 | Heinrich et al. |
| 2002/0095184 A1 | 7/2002 | Bardy et al. |
| 2002/0107544 A1 | 8/2002 | Osteroff et al. |
| 2002/0107545 A1 | 8/2002 | Rissmann et al. |
| 2003/0023175 A1 | 1/2003 | Arzbaecher et al. |
| 2003/0212436 A1 | 11/2003 | Brown |
| 2004/0172065 A1 | 9/2004 | Sih et al. |
| 2004/0215240 A1 | 10/2004 | Lovett et al. |
| 2004/0215277 A1 | 10/2004 | Osterhoff et al. |
| 2004/0243014 A1 | 12/2004 | Lee et al. |
| 2004/0260351 A1 | 12/2004 | Holmstrom et al. |
| 2005/0004612 A1 | 1/2005 | Scholten et al. |
| 2005/0010120 A1 | 1/2005 | Jung |
| 2005/0038478 A1 | 2/2005 | Klepfer et al. |
| 2005/0043895 A1 | 2/2005 | Schechter |
| 2005/0065587 A1 | 3/2005 | Gryzwa |
| 2005/0107839 A1 | 5/2005 | Sanders |
| 2005/0131477 A1 | 6/2005 | Meyer et al. |
| 2005/0131478 A1 | 6/2005 | Kim et al. |
| 2005/0131480 A1 | 6/2005 | Kramer et al. |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0116593 A1 | 6/2006 | Zhang et al. |
| 2006/0129194 A1 | 6/2006 | Zhang |
| 2006/0129196 A1 | 6/2006 | Dong et al. |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2006/0253162 A1 | 11/2006 | Zhang et al. |
| 2006/0253164 A1 | 11/2006 | Zhang et al. |
| 2006/0259086 A1 | 11/2006 | Yu et al. |
| 2007/0049974 A1 | 3/2007 | Li et al. |
| 2007/0142737 A1 | 6/2007 | Cazares et al. |
| 2008/0004665 A1 | 1/2008 | McCabe et al. |
| 2008/0009909 A1 | 1/2008 | Sathaye et al. |

| | | | |
|---|---|---|---|
| 2008/0045851 | A1 | 2/2008 | Cazares et al. |
| 2009/0076557 | A1 | 3/2009 | Zhang et al. |
| 2009/0198301 | A1 | 8/2009 | Zhang et al. |

FOREIGN PATENT DOCUMENTS

| | | |
|---|---|---|
| EP | 0560569 | 9/1993 |
| EP | 1038498 | 9/2000 |
| EP | 1291038 | 3/2003 |
| EP | 1629863 | 3/2006 |
| WO | WO9217240 | 10/1992 |
| WO | WO9220402 | 11/1992 |
| WO | WO0240097 | 5/2002 |
| WO | WO0247761 | 6/2002 |
| WO | WO02087696 | 11/2002 |
| WO | WO03003905 | 1/2003 |
| WO | WO03028550 | 4/2003 |
| WO | WO2004026398 | 4/2004 |
| WO | WO2005058412 | 6/2005 |
| WO | WO2005089865 | 9/2005 |
| WO | WO2006065707 | 6/2006 |
| WO | WO2008005270 | 1/2008 |

OTHER PUBLICATIONS

Belouchrani et al., "Blind Source Separation Based on Time-Frequency Signal Representations", IEEE Transactions on Signal Processing, vol. 46, No. 11, pp. 2888-2897, Nov. 1998.
Cohen et al. "Capture Management Efficacy in children and young adults with endocardial and unipolar epicardial systems", Europace, vol. 6, pp. 248-255, 2004.
Comon, "Independent component analysis, A new concept?", Signal Processing, vol. 36, No. 3, pp. 287-314, Apr. 1994.
Gallois, et al., "Multi-Channel Analysis of the EEG Signals and Statistic Particularities for Epileptic Seizure Forecast", Second Joint EMBS/BMES Conference, pp. 208-215, Oct. 23-26, 2002.
Gradaus et al., "Nonthoracotomy Implantable Cardioverter Defibrillator Placement in Children: Use of a Subcutaneous Array Leads and Abdominally Placed Implantable Cardioverter Defibrillators in Children", Journal of Cardiovascular Electrophysiology, vol. 12, No. 3, pp. 356-360, Mar. 2001.
Hartz et al., "New Approach to Defibrillator Insertion", Journal of Thoracic Cardiovascular Surgery, vol. 97, pp. 920-922, 1989.
Hyvärinen et al., "Independent Component Analysis: A Tutorial", Helsinki University of Technology, Apr. 1999.
Kolettis et al., "Submammary Implantation of a Cardioverter-Defibrillator with a Nonthoractomy Lead System", American Heart Journal, vol. 126, pp. 1222-1223, Nov. 1993.
Krahn, A.D. et al. "Recurrent syncope. Experience with an implantable loop record", Cardiol. Clin., vol. 15(2), May 1997, pp. 316-326. (abstract only).
Leng et al., "Lead Configuration for Defibrillator Implantation in a Patient with Congenital Heart Disease and a Mechanical Prosthetic Tricuspid Valve", PACE, vol. 24, No. 8, pp. 1291-1292, Aug. 2001.
Park et al., "Use of an Implantable Cardioverter Defibrillator in an Eight-Month-Old Infant with Ventricular Fibrillation Arising from a Myocardial Fibroma", PACE, vol. 22, No. 1, pp. 138-139, Jan. 1999.
Rieta, et al., "Atrial Activity Extraction Based on Blind Source Separation as an Alternative to QRST Cancellation for Atrial Fibrillation Analysis", Computers in Cardiology, vol. 27, pp. 69-72, 2000.
Schuder et al., "Transthoracic Ventricular Defibrillation in the Dog with Truncated and Untruncated Exponential Stimuli", IEEE Trans. On Bio-Medical Engineering, vol. BME-18, No. 6, pp. 410-415, Nov. 1971.
Schuder et al., "Ventricular Defibrillation in the Dog Using Implanted and Partially Implanted Electrode Systems", American Journal of Cardiology, vol. 33, pp. 243-247 (Feb. 1974).
Schuder et al., "Experimental Ventricular Defibrillation with an Automatic and Completely Implanted System", Trans. Am. Soc. Artif. Int. Organs, vol. 16, pp. 207-212, 1970.
Smits et al., "Defibrillation Threshold (DFT) Model of a Fully Subcutaneous ICD System", Europace Supplements, vol. 2, Jun. 2001 at col. 778, p. B83.
Splett et al. "Determination of Pacing Capture in Implantable Defibrillators: Benefit of Evoked Response Detection Using RV Coil to Can Vector," PACE, vol. 23, pp. 1645-1650, Nov. 2000.
Stirbis et al., "Optimizing the Shape of Implanted Artificial Pacemakers", Kaunas Medical Institute. Translated from Meditsinskaya Tekhnika, No. 6, pp. 25-27, 1986.
Wilkoff et al., "Preventing Shocks after ICD Implantation: Can a Strategy of Standardized ICD Programming Match Physician Tailored?", Late Breaking Trials, HRS, 2005, (no copy available).
Zarzoso et al., "Blind Separation of Independent Sources for Virtually Any Source Probability Density Function", IEEE Transactions on Signal Processing, vol. 47, No. 9, pp. 2419-2432, Sep. 1999.
Zarzoso et al., "Noninvasive Fetal Electrocardiogram Extraction: Blind Separation Versus Adaptive Noise Cancellation", IEEE Transactions on Biomedical Engineering, vol. 48, No. 1, pp. 12-18, Jan. 2001.
Office Action from U.S. Appl. No. 10/876,008 dated Aug. 31, 2007, 11 pages.
Office Action from U.S. Appl. No. 10/876,008 dated Oct. 25, 2007, 22 pages.
Office Action from U.S. Appl. No. 10/876,008 dated May 27, 2008, 11 pages.
Office Action from U.S. Appl. No. 10/876,008 dated Dec. 2, 2008, 6 pages.
Office Action from U.S. Appl. No. 10/876,008 dated May 22, 2009, 10 pages.
Office Action from U.S. Appl. No. 10/741,814 dated Aug. 1, 2006, 12 pages.
Office Action from U.S. Appl. No. 11/124,972 dated Sep. 13, 2007, 16 pages.
Office Action from U.S. Appl. No. 11/124,972 dated Mar. 26, 2008, 12 pages.
Office Action from U.S. Appl. No. 11/125,020 dated Dec. 26, 2006, 16 pages.
Office Action from U.S. Appl. No. 11/125,020 dated Jun. 7, 2007, 10 pages.
Examiner's Answer from U.S. Appl. No. 11/125,020 dated May 7, 2008, 19 pages.
Appeal Decision from U.S. Appl. No. 11/125,020 dated Nov. 9, 2009, 13 pages.
Office Action from U.S. Appl. No. 11/079,744 dated Aug. 24, 2007, 13 pages.
Office Action from U.S. Appl. No. 11/079,744 dated Feb. 21, 2008, 8 pages.
Office Action from U.S. Appl. No. 11/079,744 dated Jul. 3, 2008, 10 pages.
Office Action from U.S. Appl. No. 11/079,744 dated Feb. 11, 2009, 11 pages.
Office Action from U.S. Appl. No. 11/124,950 dated Dec. 19, 2006, 16 pages.
Office Action from U.S. Appl. No. 11/124,950 dated Jun. 7, 2007, 8 pages.
Examiner's Answer from U.S. Appl. No. 11/124,950 dated Jul. 10, 2008, 12 pages.
Appeal from U.S. Appl. No. 11/124,950 dated Nov. 12, 2009, 14 pages.
Office Action from U.S. Appl. No. 10/955,397 dated Dec. 19, 2006, 10 pages.
Office Action from U.S. Appl. No. 10/955,397 dated Jun. 7, 2007, 12 pages.
Examiner's Answer from U.S. Appl. No. 10/955,397 dated Jul. 10, 2008, 24 pages.
Appeal from U.S. Appl. No. 10/955,397 dated Nov. 12, 2009, 13 pages.
Office Action from U.S. Appl. No. 11/478,428 dated Jan. 12, 2008, 21 pages.
Office Action from U.S. Appl. No. 11/478,428 dated Jun. 1, 2009, 12 pages.
Office Action from U.S. Appl. No. 11/478,428 dated Nov. 3, 2009, 12 pages.
International Search Report and Written Opinion from International Application No. PCT/US2005/022575 dated Nov. 2, 2005, 12 pages.
International Preliminary Report on Patentability from International Application No. PCT/US2005/022575 dated Jan. 11, 2007, 7 pages.
International Preliminary Report on Patentability from International Application No. PCT/US2005/035638 dated Apr. 3, 2007, 6 pages.
International Search Report and Written Opinion from International Application No. PCT/US2005/035638 dated Feb. 27, 2006, 10 pages.

AUTOMATIC ORIENTATION DETERMINATION FOR ECG MEASUREMENTS USING MULTIPLE ELECTRODES

RELATED PATENT DOCUMENTS

This is a divisional of U.S. patent application Ser. No. 10/876,008, now U.S. Pat. No. 7,706,866, filed on Jun. 24, 2004, to which Applicant claims priority under 35 U.S.C. §120, and which is incorporated herein by reference.

FIELD OF THE INVENTION

The present invention relates generally to implantable medical devices employing cardiac signal separation and, more particularly, to cardiac sensing and/or stimulation devices employing automated vector selection from multiple electrodes.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators include one or more endocardial leads to which at least one defibrillation electrode is connected. Such implantable cardioverter/defibrillators are capable of delivering high-energy shocks to the heart, interrupting the ventricular tachyarrhythmia or ventricular fibrillation, and allowing the heart to resume normal sinus rhythm. Implantable cardioverter/defibrillators may also include pacing functionality.

SUMMARY OF THE INVENTION

The present invention is directed to cardiac monitoring and/or stimulation methods and systems that provide monitoring, defibrillation therapies, pacing therapies, or a combination of these capabilities. Embodiments of the present invention relate generally to implantable medical devices employing cardiac signal separation and, more particularly, to cardiac monitoring and/or stimulation devices employing automated vector selection from multiple electrodes.

According to an embodiment, a system of the present invention includes a housing configured for implantation in a patient and more than two electrodes each configured for sensing a composite signal. A controller is provided in the housing. The system further includes a memory and a signal processor. The memory is configured to store a target vector, and the signal processor is configured to receive a plurality of composite signals and perform a source separation algorithm that separates a target signal from the plurality of composite signals using the target vector. The signal processor is further configured to update the target vector stored in the memory by performing a subsequent source separation, such as blind source separation.

In one configuration, the signal processor and the memory are provided in the implantable housing. In another configuration, the signal processor is provided in a patient-external device or system, and the signal processor and controller are coupled to respective communication devices to facilitate wireless communication between the signal processor and controller. In a further configuration, the signal processor is provided in a network server system, and the signal processor and controller are coupled to respective communication devices to facilitate wireless communication between the signal processor and controller.

In a further embodiment of the present invention, a method of signal separation involves sensing, at least in part implantably, a plurality of composite signals using a plurality of cardiac electrodes. A source separation is performed using the detected plurality of composite signals, the source separation producing a plurality of vectors. Source separation may include blind source separation involving a principal component analysis, including singular value decomposition, and/or independent component analysis. The method further involves reconstructing, for each vector of the plurality of vectors, a signal from the detected plurality of composite signals, and selecting one vector from the plurality of vectors as a selected vector based on a selection criterion. Selection criteria may include, for example, finding a noise signal, finding a skeletal muscle signal, or finding another particular signal of interest.

According to another embodiment, a signal separation method of the present invention involves sensing, at least in part implantably, a plurality of composite signals at a plurality of locations, and performing source separation on the detected plurality of composite signals to produce a set of signal vectors. The method also involves selecting, from the set of signal vectors, a target vector associated with a target signal. The method further involves updating selection of the target vector by performing a subsequent source separation on the detected plurality of composite signals. Updating the target vector may be performed in response to a change in, for example, pathology, therapy, posture, or other change necessitating a change in vector to separate the cardiac signal.

In accordance with another embodiment, a method of signal separation involves receiving a plurality of signals from a plurality of electrodes configured to detect cardiac activity. The method further involves mathematically reconstructing an electrocardiogram vector corresponding to a signal having a largest cardiac signal-to-noise ratio using a linear combination of the plurality of signals.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
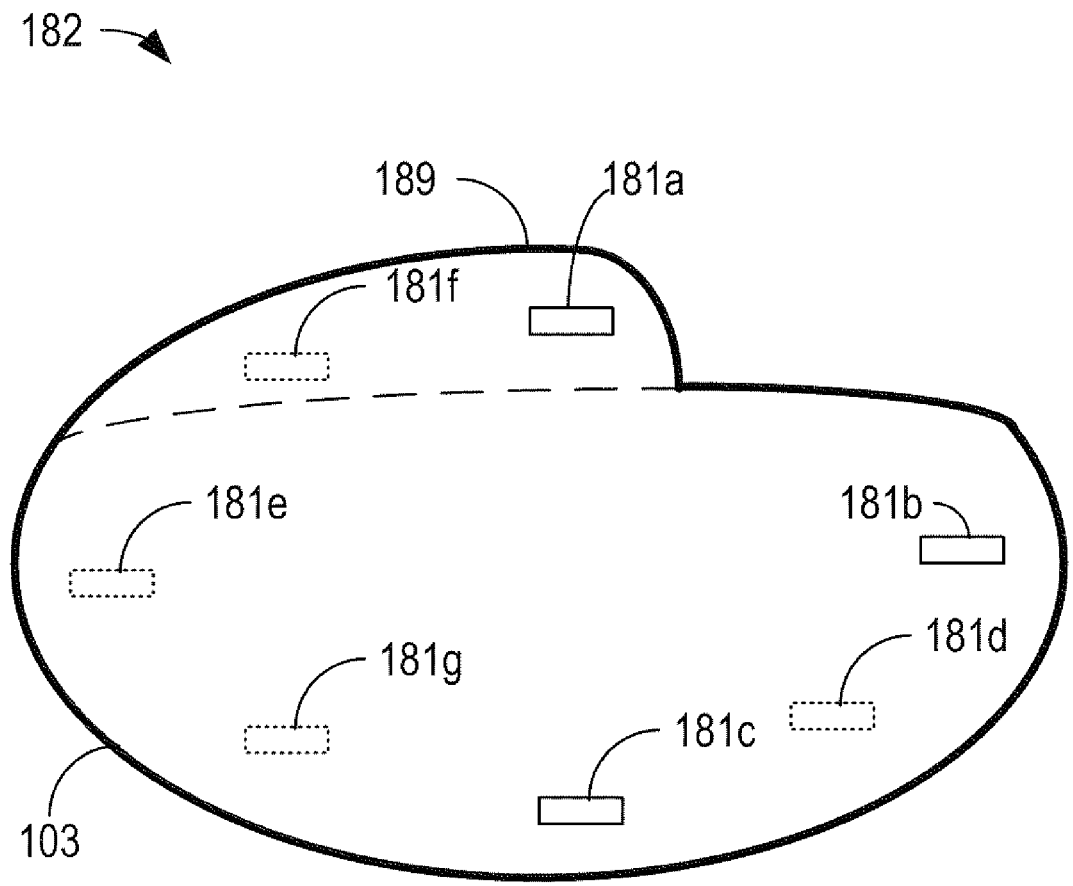
FIG. 1 is a top view of an implantable cardiac device in accordance with the present invention, having at least three electrodes.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implanted or partially implanted device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement an automated vector selection and updating methodology of the present invention. A non-limiting, representative list of such devices includes cardiac monitors, pacemakers, cardioverters, defibrillators, resynchronizers, and other cardiac sensing and therapy delivery devices. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as patient-internal medical devices (PIMD) for convenience. A PIMD implemented in accordance with the present invention may incorporate one or more of the electrode types identified above and/or combinations thereof.

In general, the quality of the electrocardiogram or electrogram sensed from one pair of electrodes of a PIMD depends on the orientation of the electrodes with respect to the depolarization wavefront produced by the heart. The quality of the electrocardiogram (ECG) sensed from the electrodes located on a PIMD is also subject to the orientation of the PIMD, and PIMD movement after implantation. Because the physiology of each patient is different, optimal electrode positioning varies from patient to patient. Moreover, optimal orientation may change due to the variation of the ECG axis caused by external electrical stimuli, movement of the implant, or pathological changes of the heart, for example.

The signal sensed on an electrode bi-pole is the projection of the ECG vector in the direction of the bi-pole. Vector selection algorithms of the present invention advantageously exploit the strong correlation of signals from a common origin (the heart) across spatially distributed electrodes. One approach involves finding the direction (vector) along which the power of the cardiac signal is maximized, and projecting the ECG signal in this optimized direction. Another approach involves finding the direction along which the signals are the most correlated, and projecting the ECG signal in this optimized direction.

This and other approaches employ more than two electrodes of varying location, and possibly of varying configuration. In one embodiment, for example, two or more electrodes can conveniently be located on the PIMD header, whereas the can of the PIMD itself may be the third electrode. In another embodiment, one electrode may be located on the PIMD header, another is the can electrode, and a third may be a PIMD antenna used for RF telemetry.

Methods of determining vector orientation in accordance with the present invention involve receiving two or more signals from three or more electrodes configured to detect cardiac activity. An electrocardiogram vector may then be mathematically reconstructed from the signals. For example, a reconstructed signal having a largest cardiac signal-to-noise ratio, using a linear combination of the plurality of signals, may be selected as having a useful vector for PIMD's in accordance with the present invention.

FIG. 1 is a top view of a PIMD 182 in accordance with the present invention, having at least three electrodes. The PIMD 182 shown in the embodiment illustrated in FIG. 1 includes a first electrode 181a, a second electrode 181b, and a third electrode 181c provided with a can 103. The PIMD 182 detects and records cardiac activity. The can 103 is illustrated as incorporating a header 189 that may be configured to facilitate removable attachment between one or more leads and the can 103. The can 103 may include any number of electrodes positioned anywhere in or on the can 103, such as optional electrodes 181d, 181e, 181f, and 181g. Each electrode pair provides one vector available for the sensing of ECG signals.

Figure 2:
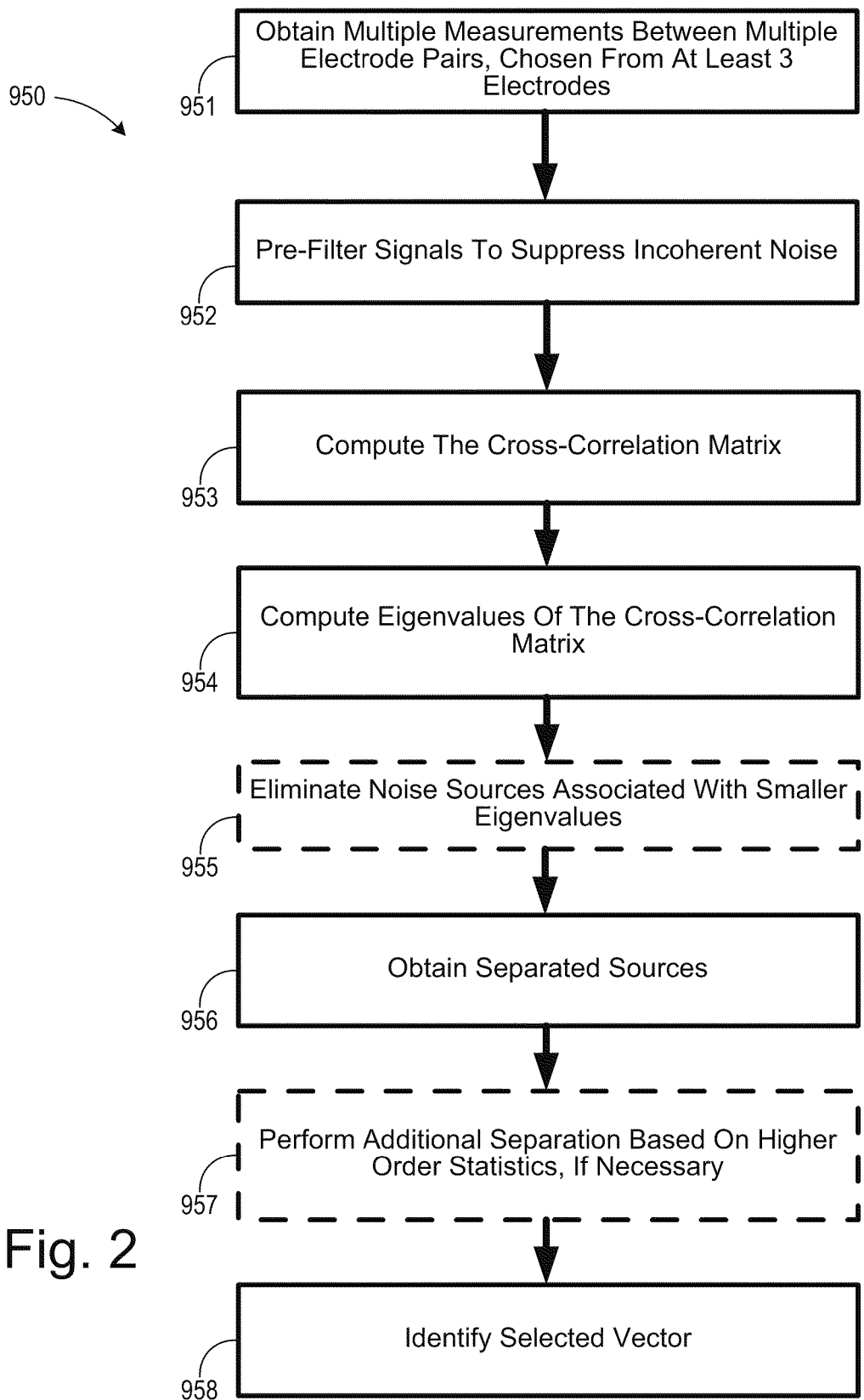
FIG. 2 is a block diagram of a vector selection process in accordance with the present invention.

FIG. 2 is a block diagram of a vector selection process 950 in accordance with the present invention. The vector selection process 950 starts at block 951, where multiple concurrent measurements are obtained between multiple respective electrode pairs, chosen from at least three electrodes. Block 952 provides for pre-filtering the collected signals with, for example, a linear-phase filter to suppress broadly incoherent noise, and to generally maximize the signal-to-noise ratio.

Block 953 indicates the computation of the cross-correlation matrix, which may be averaged over a relatively short time interval, such as about 1 second. This block enhances the components that are mutually correlated. Block 954 is then provided for computation of the eigenvalues of the cross-correlation matrix. The smaller eigenvalues, normally associated with noise, may then be used at block 955 to eliminate noise, by removing the noise components of the composite signals associated with those eigenvalues.

At block 956, signals may be separated from the composite signals using the eigenvalues. Separated sources may be obtained by taking linear combinations of the recorded signals, as specified in the eigenvectors corresponding to the larger eigenvalues. Optionally, block 957 provides for performing additional separation based on higher order statistics, if the cardiac signal is not found among the signals separated at block 956.

At block 958, the optimized cardiac signal may be identified based on the selection criteria, along with its associated vector, among the separated signals. Typically, the signal is found among the signals associated with the largest eigenvalues.

Figure 3:
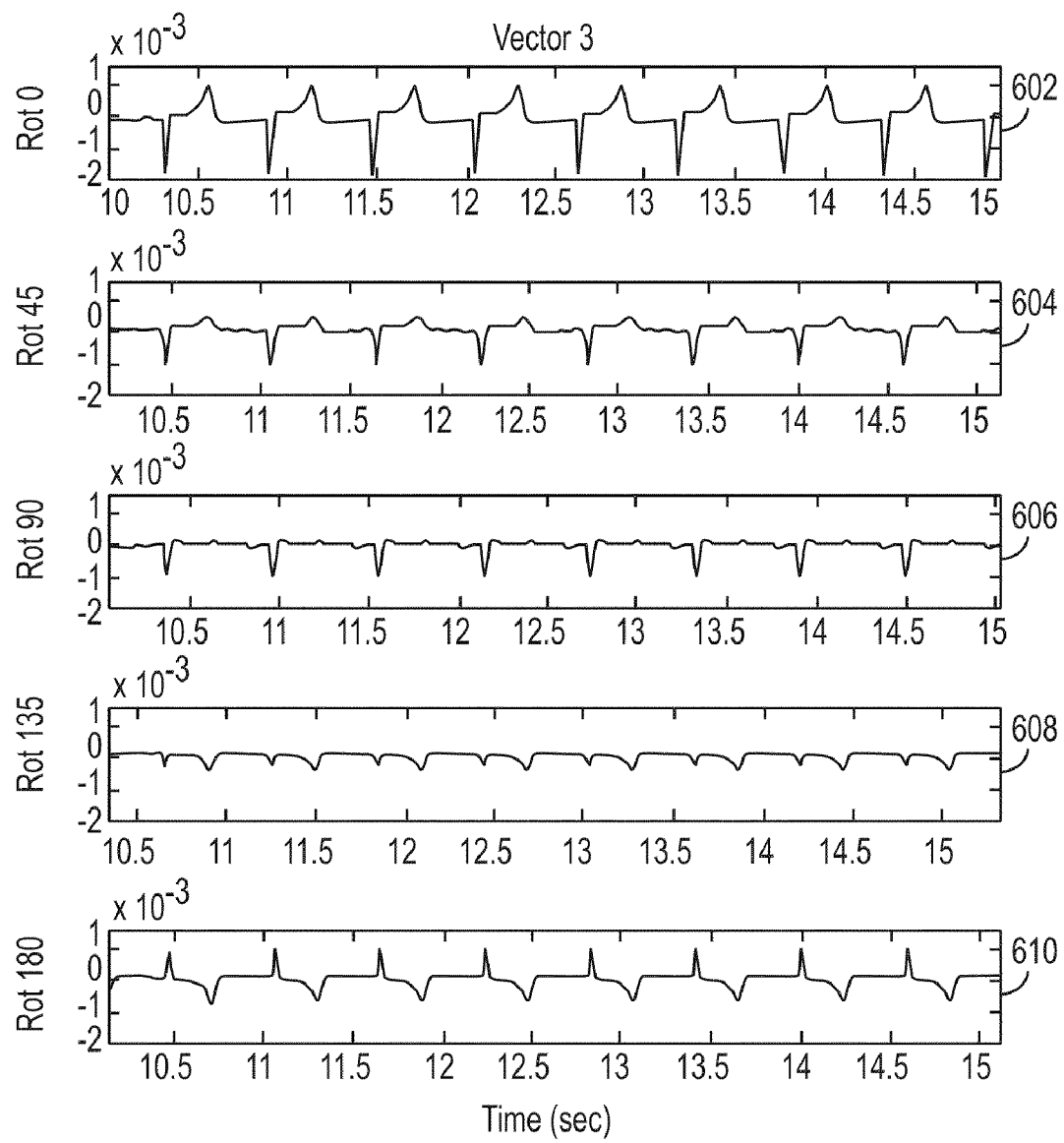
FIG. 3 is a graph illustrating one of the raw signals at five different orientations.
Figure 4:
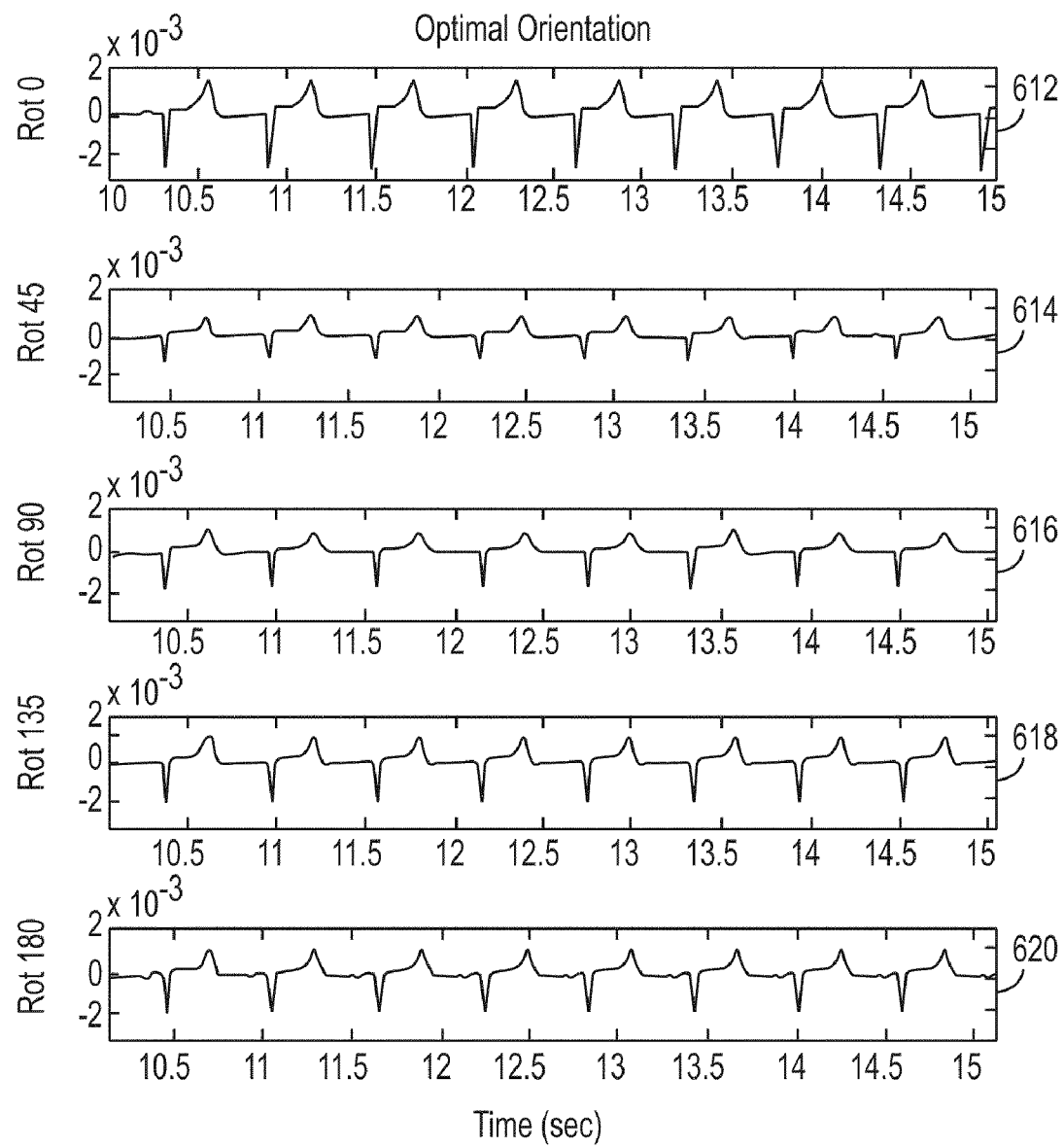
FIG. 4 is a graph illustrating selected vector oriented signals at the same five orientations illustrated in FIG. 3 in accordance with the present invention.

FIGS. 3 and 4 illustrate the result of performing the process illustrated in FIG. 2 on signals associated with vectors at five angular positions relative to an arbitrary 0 degree orientation. Experimental data were gathered from three disc electrodes oriented at five different rotations. In FIG. 3, the third signal from each rotation is shown. Angular rotation 0 is illustrated as a trace 602, angular rotation 45 degrees is illustrated as a trace 604, angular rotation 90 degrees is illustrated as a trace 606, angular rotation 135 degrees is illustrated as a trace 608, and angular rotation 180 degrees is illustrated as a trace 610. The cardiac signal is most evident in trace 602, but may be detected by the peaks evident in most traces. Angular rotation 135 of the trace 608 is the rotation with the smallest level of cardiac signal, corresponding to a vector approximately parallel to the depolarization wavefront.

FIG. 4 represents the resulting target signal at each rotation, after performing the method 950 represented in FIG. 2 on the raw data represented by FIG. 3. In FIG. 4, angular rotation 0 is illustrated as a trace 612, angular rotation 45 degrees is illustrated as a trace 614, angular rotation 90 degrees is illustrated as a trace 616, angular rotation 135 degrees is illustrated as a trace 618, angular rotation 180 degrees is illustrated as a trace 620. Evident in all traces, but most obvious when comparing the trace 608 of FIG. 3 with the trace 618 of FIG. 4, the cardiac signal is significantly more pronounced when applying the method 950 in accordance with the present invention.

For purposes of illustration, and not of limitation, various embodiments of devices that may use vector selection and orientation in accordance with the present invention are described herein in the context of PIMD's that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. Publication No. 2004/0230230 and U.S. Pat. Nos. 7,299,086 and 7,499,750, which are hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of a type that may benefit from electrode orientation and vector selection and updating methods and implementations are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of a type that may benefit from electrode orientation and vector selection and updating methods and implementations are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of a type that may benefit from electrode orientation and vector selection and updating methods and implementations are disclosed in commonly owned U.S. Pat. Nos. 5,313,953; 5,388,578; and 5,411,031, which are hereby incorporated herein by reference.

Various embodiments described herein may be used in connection with congestive heart failure (CHF) monitoring, diagnosis, and/or therapy. A PIMD of the present invention may incorporate CHF features involving dual-chamber or bi-ventricular pacing/therapy, cardiac resynchronization therapy, cardiac function optimization, or other CHF related methodologies. For example, any PIMD of the present invention may incorporate features of one or more of the following references: commonly owned U.S. Pat. Nos. 7,260,432; 6,411,848; 6,285,907; 4,928,688; 6,459,929; 5,334,222; 6,026,320; 6,371,922; 6,597,951; 6,424,865; and 6,542,775, each of which is hereby incorporated herein by reference.

A PIMD may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 5:
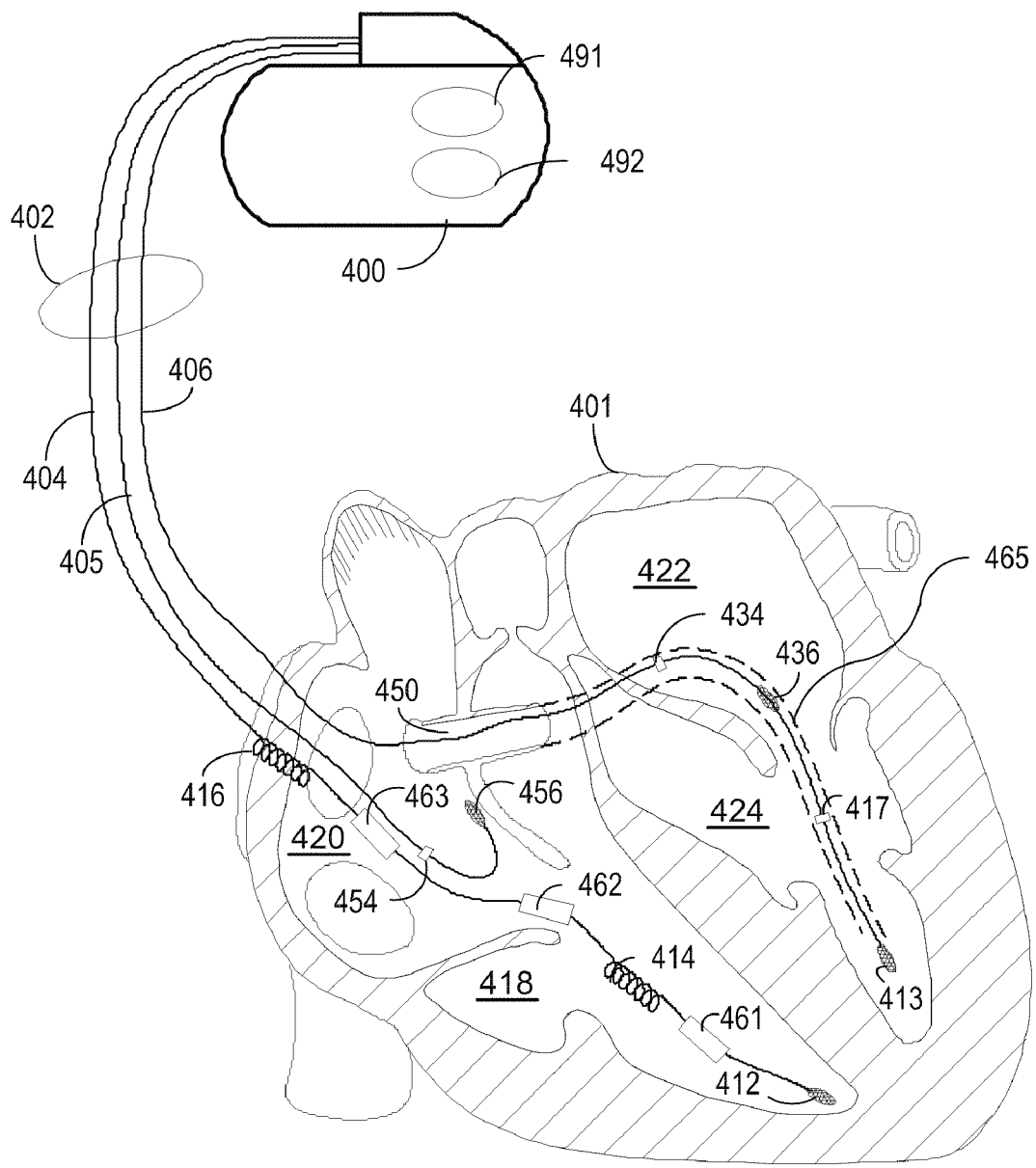
FIG. 5 is an illustration of an implantable cardiac device including a lead assembly shown implanted in a sectional view of a heart, in accordance with embodiments of the invention.

Referring now to FIG. 5, the implantable device illustrated in FIG. 5 is an embodiment of a PIMD including a cardiac rhythm management (CRM) device with an implantable pacemaker/defibrillator 400 electrically and physically coupled to an intracardiac lead system 402. The intracardiac lead system 402 is implanted in a human body with portions of the intracardiac lead system 402 inserted into a heart 401. Electrodes of the intracardiac lead system 402 may be used to detect and analyze cardiac signals produced by the heart 401 and to provide stimulation and/or therapy energy to the heart 401 under predetermined conditions, to treat cardiac arrhythmias of the heart 401.

The CRM 400 depicted in FIG. 5 is a multi-chamber device, capable of sensing signals from one or more of the right and left atria 420, 422 and the right and left ventricles 418, 424 of the heart 401 and providing pacing pulses to one or more of the right and left atria 420, 422 and the right and left ventricles 418, 424. Low energy pacing pulses may be delivered to the heart 401 to regulate the heart beat or maintain a cardiac rhythm, for example. In a configuration that includes cardioversion/defibrillation capabilities, high energy pulses may also be delivered to the heart 401 if an arrhythmia is detected that requires cardioversion or defibrillation.

The intracardiac lead system 402 includes a right ventricular lead system 404, a right atrial lead system 405, and a left atrial/ventricular lead system 406. The right ventricular lead system 404 includes an RV-tip pace/sense electrode 412, an RV-coil electrode 414, and one or more electrodes 461, 462, 463 suitable for measuring transthoracic impedance. In one arrangement, impedance sense and drive electrodes 461, 462, 463 are configured as ring electrodes. The impedance drive electrode 461 may be located, for example, in the right ventricle 418. The impedance sense electrode 462 may be located in the right atrium 420. Alternatively or additionally, an impedance sense electrode 463 may be located in the superior right atrium 420 or near the right atrium 420 within the superior vena cava.

The RV-tip electrode 412 is positioned at an appropriate location within the right ventricle 418 for pacing the right ventricle 418 and sensing cardiac activity in the right ventricle 418. The right ventricular lead system may also include one or more defibrillation electrodes 414, 416, positioned, for example, in the right ventricle 418 and the superior vena cava, respectively.

The atrial lead system 405 includes A-tip and A-ring cardiac pace/sense electrodes 456, 454. In the configuration of FIG. 5, the intracardiac lead system 402 is positioned within the heart 401, with a portion of the atrial lead system 405 extending into the right atrium 420. The A-tip and A-ring electrodes 456, 454 are positioned at an appropriate location within the right atrium 420 for pacing the right atrium 420 and sensing cardiac activity in the right atrium 420.

The lead system 402 illustrated in FIG. 5 also includes a left atrial/left ventricular lead system 406. The left atrial/left ventricular lead system 406 may include, one or more electrodes 434, 436, 417, 413 positioned within a coronary vein 465 of the heart 401. Additionally, or alternatively, one or more electrodes may be positioned in a middle cardiac vein, a left posterior vein, a left marginal vein, a great cardiac vein or an anterior vein.

The left atrial/left ventricular lead system 406 may include one or more endocardial pace/sense leads that are advanced through the superior vena cava (SVC), the right atrium 420, the valve of the coronary sinus, and the coronary sinus 450 to locate the LA-tip 436, LA-ring 434, LV-tip 413 and LV-ring 417 electrodes at appropriate locations adjacent to the left atrium 422 and left ventricle 424, respectively. In one example, lead placement involves creating an opening in a percutaneous access vessel, such as the left subclavian or left cephalic vein. For example, the lead system 402 may be guided into the right atrium 420 of the heart via the superior vena cava.

From the right atrium 420, the left atrial/left ventricular lead system 406 is deployed into the coronary sinus ostium, the opening of the coronary sinus 450. The left atrial/left ventricular lead system 406 is guided through the coronary sinus 450 to a coronary vein of the left ventricle 424. This vein is used as an access pathway for leads to reach the surfaces of the left atrium 422 and the left ventricle 424 which are not directly accessible from the right side of the heart. Lead placement for the left atrial/left ventricular lead system 406 may be achieved via subclavian vein access. For example, a preformed guiding catheter may be used for insertion of the LV and LA electrodes 413, 417, 436, 434 adjacent the left ventricle 424 and left atrium 422, respectively.

Lead placement for the left atrial/left ventricular lead system 406 may be achieved via the subclavian vein access and a preformed guiding catheter for insertion of the LV and LA electrodes 413, 417, 436, 434 adjacent the left ventricle 424 and left atrium 422, respectively. In one configuration, the left atrial/left ventricular lead system 406 is implemented as a single-pass lead. It is understood that the descriptions in the preceding paragraphs with regard to LV-tip 413 and LV-ring 417 electrodes are equally applicable to a lead configuration employing distal and proximal LV ring electrodes (with no LV-tip electrode).

Additional configurations of sensing, pacing and defibrillation electrodes may be included in the intracardiac lead system 402 to allow for various sensing, pacing, and defibrillation capabilities of multiple heart chambers. In other configurations, the intracardiac lead system 402 may have only a single lead with electrodes positioned in the right atrium or the right ventricle to implement single chamber cardiac pacing. In yet other embodiments, the intracardiac lead system 402 may not include the left atrial/left ventricular lead 406 and may support pacing and sensing of the right atrium and right ventricle only. Any intracardiac lead and electrode arrangements and configurations are considered to be within the scope of the present system in accordance with embodiments of the invention.

A PIMD may incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference.

Figure 6:
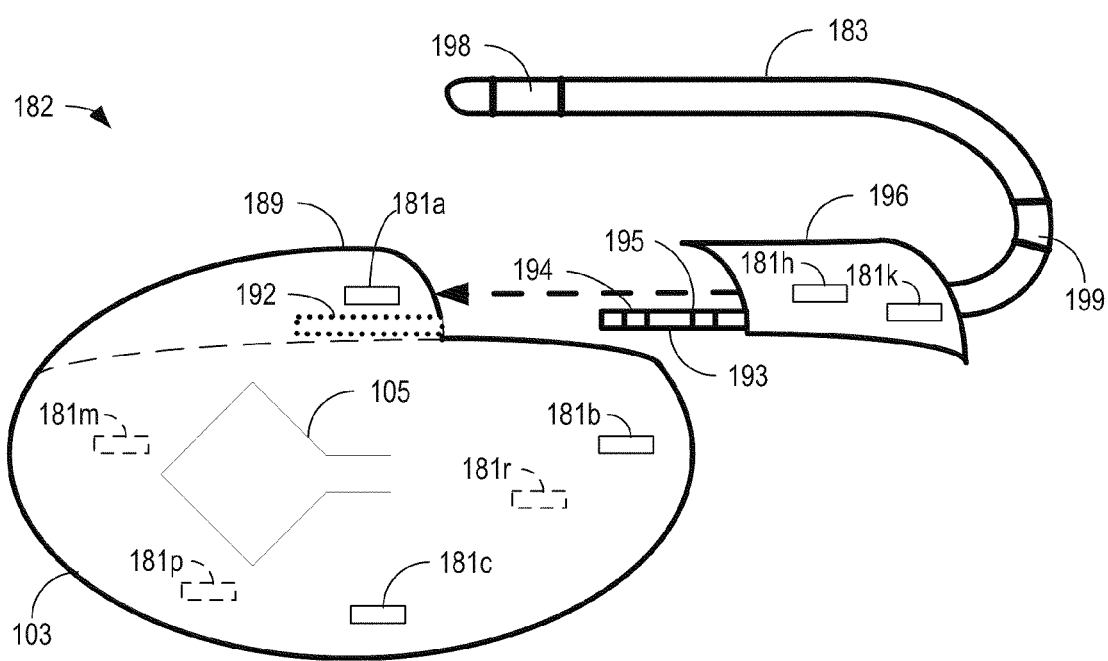
FIG. 6 is a top view of an implantable cardiac device in accordance with the present invention, including an antenna electrode and a lead/header arrangement.

FIG. 6 is a top view of a PIMD 182 in accordance with the present invention, having at least three electrodes. One electrode is illustrated as an antenna 105 of the PIMD that may also be used for RF communications. The PIMD 182 shown in the embodiment illustrated in FIG. 6 includes a first electrode 198 and a second electrode 199 coupled to a can 103 through a header 189, via an electrode module 196. The first electrode 198 and second electrode 199 may be located on a lead 183 (single or multiple lead, or electrode array), or may be located directly in or on the electrode module 196.

The PIMD 182 detects and records cardiac activity. The can 103 is illustrated as incorporating the header 189. The header 189 may be configured to facilitate removable attachment between an electrode module 196 and the can 103, as is shown in the embodiment depicted in FIG. 6. The header 189 includes a female coupler 192 configured to accept a male coupler 193 from the electrode module 196. The male coupler 193 is shown having two electrode contacts 194, 195 for coupling one or more electrodes 198,199 through the electrode module 196 to the can 103. An electrode 181$h$ and an electrode 181$k$ are illustrated on the header 189 of the can 103 and may also be coupled through the electrode module 196 to the can 103. The can 103 may alternatively, or in addition to the header electrodes 181$h$, 181$k$ and/or first and second electrodes 198, 199, include one or more can electrodes 181$a$, 181$b$, 181$c$.

Electrodes may also be provided on the back of the can 103, typically the side facing externally relative to the patient after implantation. For example, electrodes 181$m$, 181$p$, and 181$r$ are illustrated as positioned in or on the back of the can 103. Providing electrodes on both front and back surfaces of the can 103 provides for a three-dimensional spatial distribution of the electrodes, which may provide additional discrimination capabilities from vector selection methods in accordance with the present invention. Further description of three-dimensional configurations are described in U.S. Pat. No. 7,299,086, previously incorporated by reference.

In this and other configurations, the header 189 incorporates interface features (e.g., electrical connectors, ports, engagement features, and the like) that facilitate electrical connectivity with one or more lead and/or sensor systems, lead and/or sensor modules, and electrodes. The header 189 may also incorporate one or more electrodes in addition to, or instead of, the electrodes provided by the lead 183, such as electrodes 181$h$ and 181$k$, to provide more available vectors to the PIMD. The interface features of the header 189 may be protected from body fluids using known techniques.

The PIMD 182 may further include one or more sensors in or on the can 103, header 189, electrode module 196, or lead(s) that couple to the header 189 or electrode module 196. Useful sensors may include electrophysiologic and non-electrophysiologic sensors, such as an acoustic sensor, an impedance sensor, a blood sensor, such as an oxygen saturation sensor (oximeter or plethysmographic sensor), a blood pressure sensor, minute ventilation sensor, or other sensor described or incorporated herein.

Figure 7:
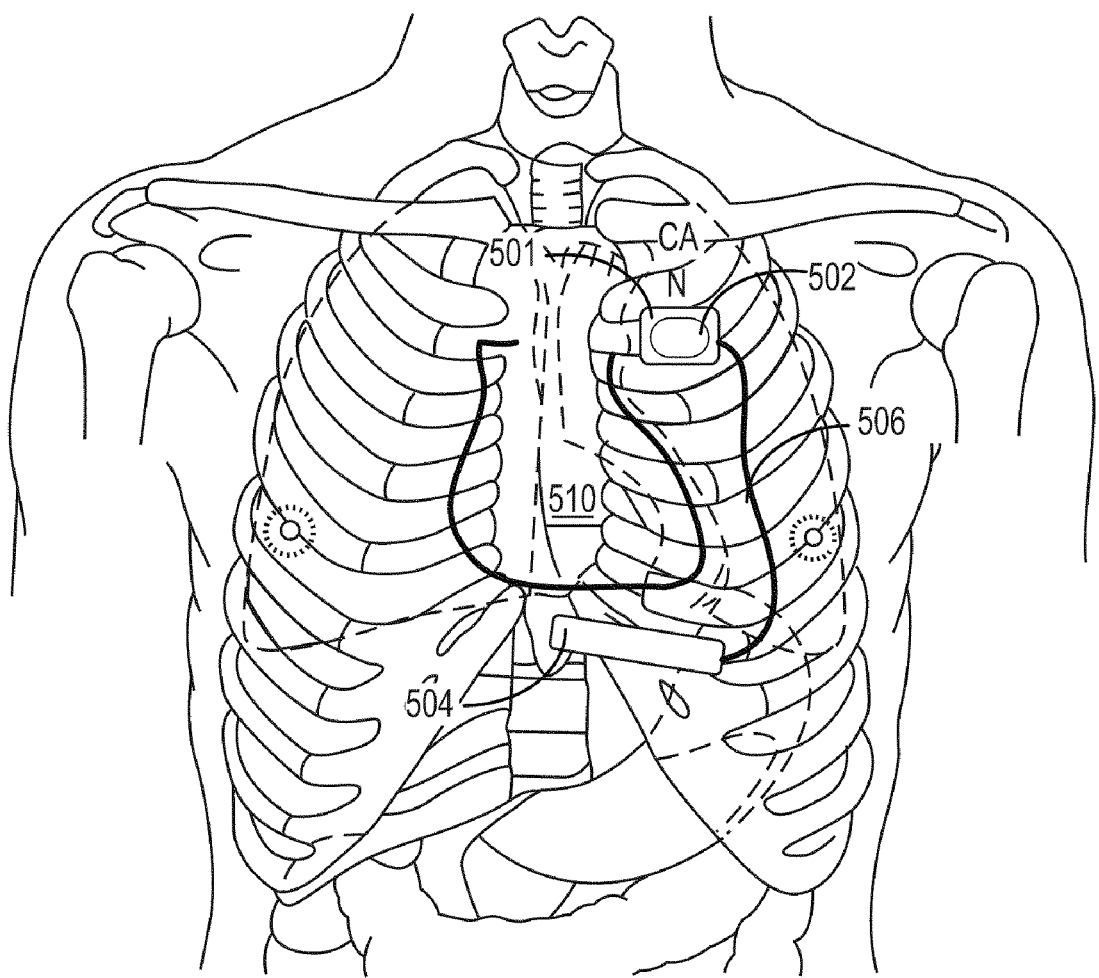
FIG. 7 is a diagram illustrating components of a cardiac monitoring and/or stimulation device including an electrode array in accordance with an embodiment of the present invention.

In one configuration, as is illustrated in FIG. 7, electrode subsystems of a PIMD system are arranged about a patient's heart 510. The PIMD system includes a first electrode subsystem, comprising a can electrode 502, and a second electrode subsystem 504 that includes at least two electrodes or at least one multi-element electrode. The second electrode subsystem 504 may include a number of electrodes used for sensing and/or electrical stimulation.

In various configurations, the second electrode subsystem 504 may include a combination of electrodes. The combination of electrodes of the second electrode subsystem 504 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 502 is positioned on the housing 501 that encloses the PIMD electronics. In one embodiment, the can electrode 502 includes the entirety of the external surface of housing 501. In other embodiments, various portions of the housing 501 may be electrically isolated from the can electrode 502 or from tissue. For example, the active area of the can electrode 502 may include all or a portion of either the anterior or posterior surface of the housing 501 to direct current flow in a manner advantageous for cardiac sensing and/or stimulation.

Portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

Figure 8:
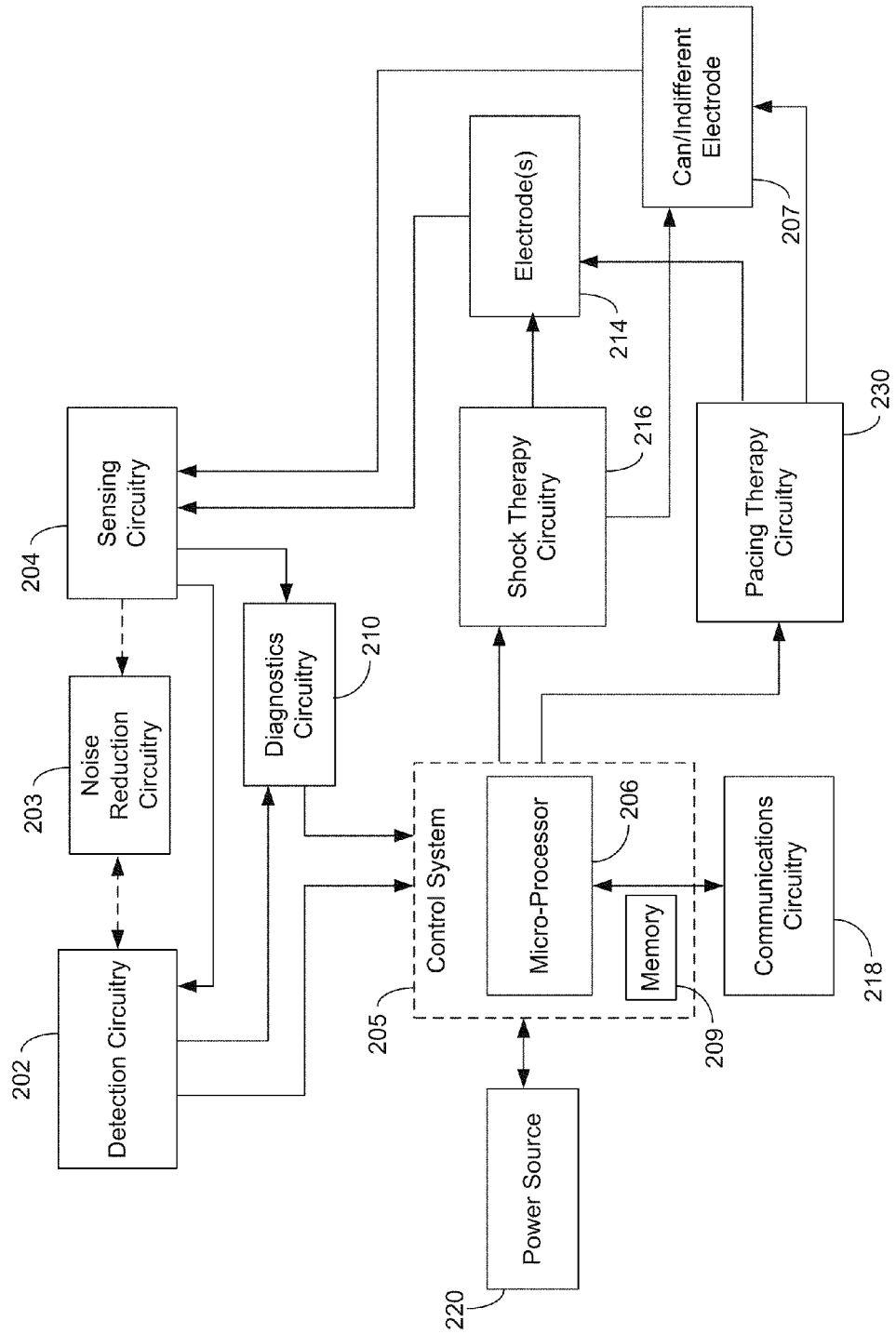
FIG. 8 is a block diagram illustrating various components of a cardiac monitoring and/or stimulation device in accordance with an embodiment of the present invention.

FIG. 8 is a block diagram depicting various componentry of different arrangements of a PIMD in accordance with embodiments of the present invention. The components, functionality, and configurations depicted in FIG. 8 are intended to provide an understanding of various features and combinations of features that may be incorporated in a PIMD. It is understood that a wide variety of device configurations are contemplated, ranging from relatively sophisticated to relatively simple designs. As such, particular PIMD configurations may include some componentry illustrated in FIG. 8, while excluding other componentry illustrated in FIG. 8.

Illustrated in FIG. 8 is a processor-based control system 205 which includes a micro-processor 206 coupled to appropriate memory (volatile and/or non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. The control system 205 and associated components also provide pacing therapy to the heart. The electrical energy delivered by the PIMD may be in the form of low energy pacing pulses or high-energy pulses for cardioversion or defibrillation.

Cardiac signals are sensed using the electrode(s) 214 and the can or indifferent electrode 207 provided on the PIMD housing. Cardiac signals may also be sensed using only the electrode(s) 214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after sensing circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204 and noise reduction circuitry 203 may be useful to minimize the necessary componentry and lower the power requirements of the system.

In the illustrative configuration shown in FIG. 8, the detection circuitry 202 is coupled to, or otherwise incorporates, noise reduction circuitry 203. The noise reduction circuitry 203 operates to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise, including signal separation techniques incorporating combinations of electrodes and multi-element electrodes, are described hereinbelow.

Detection circuitry 202 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the PIMD may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the electrode(s) 214 and the can or indifferent electrode 207 of the PIMD housing.

Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of PIMD high energy delivery circuitry, structures and functionality, aspects of which may be incorporated in a PIMD of a type that may benefit from aspects of the present invention are disclosed in commonly owned U.S. Pat. Nos. 5,372,606; 5,411,525; 5,468,254; and 5,634,938, which are hereby incorporated herein by reference.

Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference.

In accordance with another configuration, a PIMD may incorporate a cardiac pacing capability in addition to, or to the exclusion of, cardioversion and/or defibrillation capabilities. As is shown in FIG. 8, the PIMD includes pacing therapy circuitry 230 that is coupled to the control system 205 and the electrode(s) 214 and can/indifferent electrodes 207. Upon command, the pacing therapy circuitry 230 delivers pacing pulses to the heart in accordance with a selected pacing therapy.

Control signals, developed in accordance with a pacing regimen by pacemaker circuitry within the control system 205, are initiated and transmitted to the pacing therapy circuitry 230 where pacing pulses are generated. A pacing regimen, such as those discussed and incorporated herein, may be modified by the control system 205. In one particular application, a sense vector optimization approach of the present invention may be implemented to enhance capture detection and/or capture threshold determinations, such as by selecting an optimal vector for sensing an evoked response resulting from application of a capture pacing stimulus.

The PIMD shown in FIG. 8 may be configured to receive signals from one or more physiologic and/or non-physiologic sensors. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Communications circuitry 218 is coupled to the microprocessor 206 of the control system 205. The communications circuitry 218 allows the PIMD to communicate with one or more receiving devices or systems situated external to the PIMD. By way of example, the PIMD may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the PIMD via the communications circuitry 218. It is noted that physiologic or non-physiologic sensors equipped with wireless transmitters or transceivers may communicate with a receiving system external of the patient.

The communications circuitry 218 preferably allows the PIMD to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the PIMD and the programmer unit during and after implant. Using a programmer, a physician is able to set or modify various parameters used by the PIMD. For example, a physician may set or modify parameters affecting sensing, detection, pacing, and defibrillation functions of the PIMD, including pacing and cardioversion/defibrillation therapy modes.

Typically, the PIMD is encased and hermetically sealed in a housing suitable for implanting in a human body as is known in the art. Power to the PIMD is supplied by an electrochemical power source 220 housed within the PIMD. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The PIMD may, in addition to a rechargeable power source, include a non-rechargeable battery. It is understood that a rechargeable power source need not be used, in which case a long-life non-rechargeable battery is employed.

The detection circuitry 202, which is coupled to a microprocessor 206, may be configured to incorporate, or communicate with, specialized circuitry for processing sensed cardiac signals in manners particularly useful in a cardiac sensing and/or stimulation device. As is shown by way of example in FIG. 8, the detection circuitry 202 may receive information from multiple physiologic and non-physiologic sensors.

The detection circuitry 202 may also receive information from one or more sensors that monitor skeletal muscle activity. In addition to cardiac activity signals, electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise.

The components, functionality, and structural configurations depicted herein are intended to provide an understanding of various features and combination of features that may be incorporated in a PIMD. It is understood that a wide variety of PIMDs and other implantable cardiac monitoring and/or stimulation device configurations are contemplated, ranging from relatively sophisticated to relatively simple designs. As such, particular PIMD or cardiac monitoring and/or stimulation device configurations may include particular features as described herein, while other such device configurations may exclude particular features described herein.

The PIMD may detect a variety of physiological signals that may be used in connection with various diagnostic, therapeutic or monitoring implementations. For example, the PIMD may include sensors or circuitry for detecting respiratory system signals, cardiac system signals, and signals related to patient activity. In one embodiment, the PIMD senses intrathoracic impedance, from which various respiratory parameters may be derived, including, for example, respiratory tidal volume and minute ventilation. Sensors and associated circuitry may be incorporated in connection with a PIMD for detecting one or more body movement or body posture or position related signals. For example, accelerometers and GPS devices may be employed to detect patient activity, patient location, body orientation, or torso position.

Figure 9:
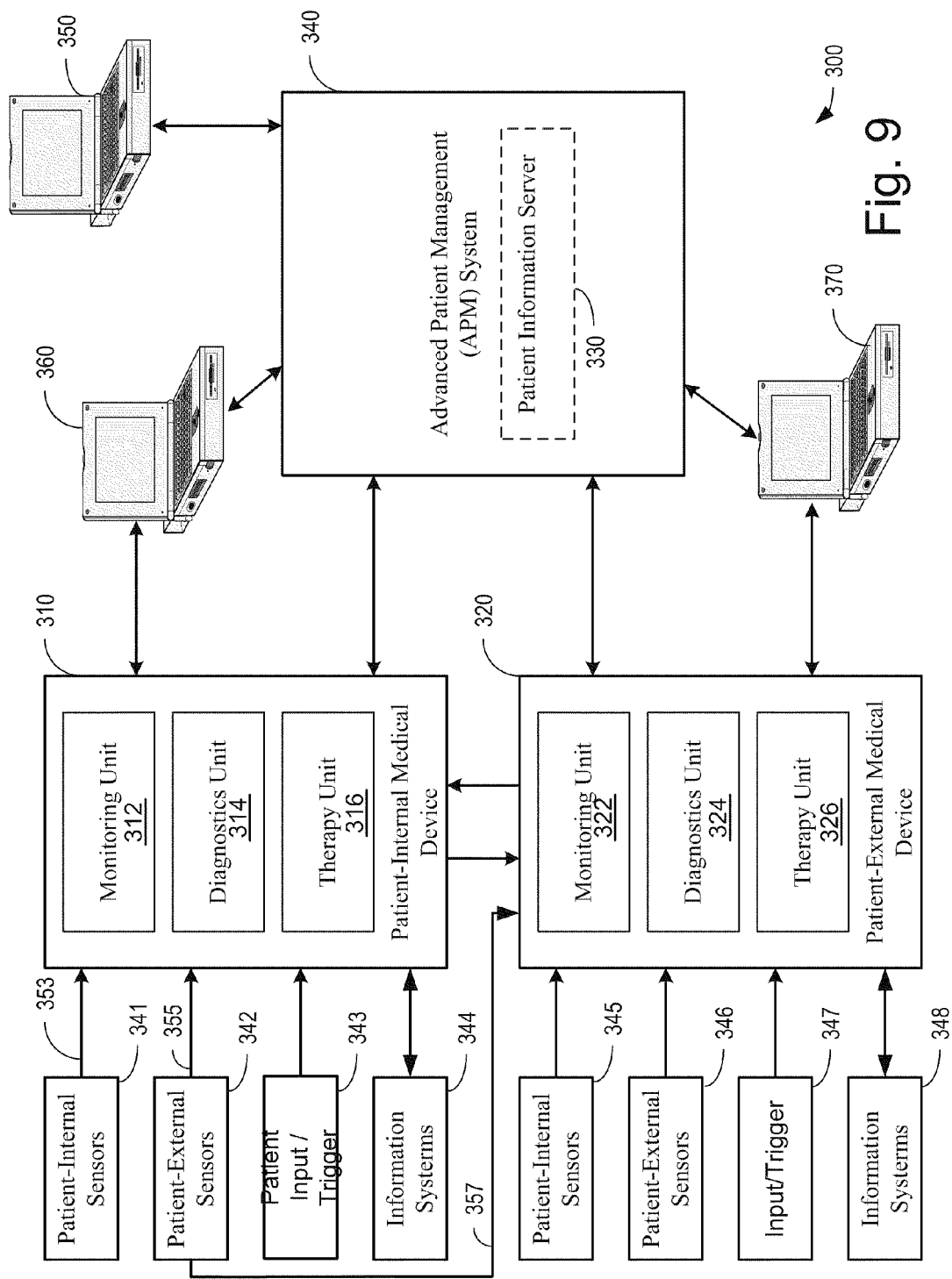
FIG. 9 is a block diagram of a medical system that may be used to implement system updating, coordinated patient monitoring, diagnosis, and/or therapy in accordance with embodiments of the present invention.

Referring now to FIG. 9, a PIMD of the present invention may be used within the structure of an advanced patient management (APM) system 300. The advanced patient management system 300 allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 9, the medical system 300 may be used to implement coordinated patient measuring and/or monitoring, diagnosis, and/or therapy in accordance with embodiments of the invention. The medical system 300 may include, for example, one or more patient-internal medical devices 310, such as a PIMD, and one or more patient-external medical devices 320, such as a monitor or signal display device. Each of the patient-internal 310 and patient-external 320 medical devices may include one or more of a patient monitoring unit 312, 322, a diagnostics unit 314, 324, and/or a therapy unit 316, 326.

The patient-external medical device 320 performs monitoring, and/or diagnosis and/or therapy functions external to the patient (i.e., not invasively implanted within the patient's body). The patient-external medical device 320 may be positioned on the patient, near the patient, or in any location external to the patient.

The patient-internal and patient-external medical devices 310, 320 may be coupled to one or more sensors 341, 342, 345, 346, patient input/trigger devices 343, 347 and/or other information acquisition devices 344, 348. The sensors 341, 342, 345, 346, patient input/trigger devices 343, 347, and/or other information acquisition devices 344, 348 may be employed to detect conditions relevant to the monitoring, diagnostic, and/or therapeutic functions of the patient-internal and patient-external medical devices 310, 320.

The medical devices 310, 320 may each be coupled to one or more patient-internal sensors 341, 345 that are fully or partially implantable within the patient. The medical devices 310, 320 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 341 may be coupled to the patient-internal medical device 310 through one or more internal leads 353. Still referring to FIG. 9, one or more patient-internal sensors 341 may be equipped with transceiver circuitry to support wireless communications between the one or more patient-internal sensors 341 and the patient-internal medical device 310 and/or the patient-external medical device 320.

The patient-external sensors 342 may be coupled to the patient-internal medical device 310 and/or the patient-external medical device 320 through one or more internal leads 355 or through wireless connections. Patient-external sensors 342 may communicate with the patient-internal medical device 310 wirelessly. Patient-external sensors 342 may be coupled to the patient-external medical device 320 through one or more internal leads 357 or through a wireless link.

In an embodiment of the present invention, the patient-external medical device 320 includes a visual display configured to simultaneously display non-electrophysiological signals and ECG signals. For example, the display may present the information visually. The patient-external medical device 320 may also, or alternately, provide signals to other components of the medical system 300 for presentation to a clinician, whether local to the patient or remote to the patient.

Referring still to FIG. 9, the medical devices 310, 320 may be connected to one or more information acquisition devices 344, 348, such as a database that stores information useful in connection with the monitoring, diagnostic, or therapy functions of the medical devices 310, 320. For example, one or more of the medical devices 310, 320 may be coupled through a network to a patient information server 330.

The input/trigger devices 343, 347 are used to allow the physician, clinician, and/or patient to manually trigger and/or transfer information to the medical devices 310, 320. The input/trigger devices 343, 347 may be particularly useful for inputting information concerning patient perceptions, such as a perceived cardiac event, how well the patient feels, and other information not automatically sensed or detected by the medical devices 310, 320. For example, the patient may trigger the input/trigger device 343 upon perceiving a cardiac event. The trigger may then initiate the recording of cardiac signals and/or other sensor signals in the patient-internal device 310. Later, a clinician may trigger the input/trigger device 347, initiating the transfer of the recorded cardiac and/or other signals from the patient-internal device 310 to the patient-external device 320 for display and diagnosis. The input/trigger device 347 may also be used by the patient, clinician, and/or physician as an activation stimulus to the PIMD to update and/or select a vector.

In one embodiment, the patient-internal medical device 310 and the patient-external medical device 320 may communicate through a wireless link between the medical devices 310, 320. For example, the patient-internal and patient-external medical devices 310, 320 may be coupled through a short-range radio link, such as Bluetooth, IEEE 802.11, and/or a proprietary wireless protocol. The communications link may facilitate uni-directional or bi-directional communication between the patient-internal 310 and patient-external 320 medical devices. Data and/or control signals may be transmitted between the patient-internal 310 and patient-external 320 medical devices to coordinate the functions of the medical devices 310, 320.

In another embodiment, patient data may be downloaded from one or more of the medical devices periodically or on command, and stored at the patient information server 330. The physician and/or the patient may communicate with the medical devices and the patient information server 330, for example, to acquire patient data or to initiate, terminate or modify recording and/or therapy.

The data stored on the patient information server 330 may be accessible by the patient and the patient's physician through one or more terminals 350, e.g., remote computers located in the patient's home or the physician's office. The patient information server 330 may be used to communicate to one or more of the patient-internal and patient-external medical devices 310, 320 to provide remote control of the monitoring, diagnosis, and/or therapy functions of the medical devices 310, 320.

In one embodiment, the patient's physician may access patient data transmitted from the medical devices 310, 320 to the patient information server 330. After evaluation of the patient data, the patient's physician may communicate with one or more of the patient-internal or patient-external devices 310, 320 through an APM system 340 to initiate, terminate, or modify the monitoring, diagnostic, and/or therapy functions of the patient-internal and/or patient-external medical systems 310, 320.

In another embodiment, the patient-internal and patient-external medical devices 310, 320 may not communicate directly, but may communicate indirectly through the APM system 340. In this embodiment, the APM system 340 may operate as an intermediary between two or more of the medical devices 310, 320. For example, data and/or control information may be transferred from one of the medical devices 310, 320 to the APM system 340. The APM system 340 may transfer the data and/or control information to another of the medical devices 310, 320.

In one embodiment, the APM system 340 may communicate directly with the patient-internal and/or patient-external medical devices 310, 320. In another embodiment, the APM system 340 may communicate with the patient-internal and/or patient-external medical devices 310, 320 through medical device programmers 360, 370 respectively associated with each medical device 310, 320. As was stated previously, the patient-internal medical device 310 may take the form of an implantable PIMD.

In accordance with one approach of the present invention, a PIMD may be implemented to separate cardiac signals for selection of vectors in a robust manner using a blind source separation (BSS) technique. It is understood that all or certain aspects of the BSS technique described below may be implemented in a device or system (implantable or non-implantable) other than a PIMD, and that the description of BSS techniques implemented in a PIMD is provided for purposes of illustration, and not of limitation. For example, algorithms that implement a BSS technique as described below may be implemented for use by an implanted processor or a non-implanted processor, such as a processor of a programmer or computer of a patient-external device communicatively coupled to the PIMD.

Figure 10:
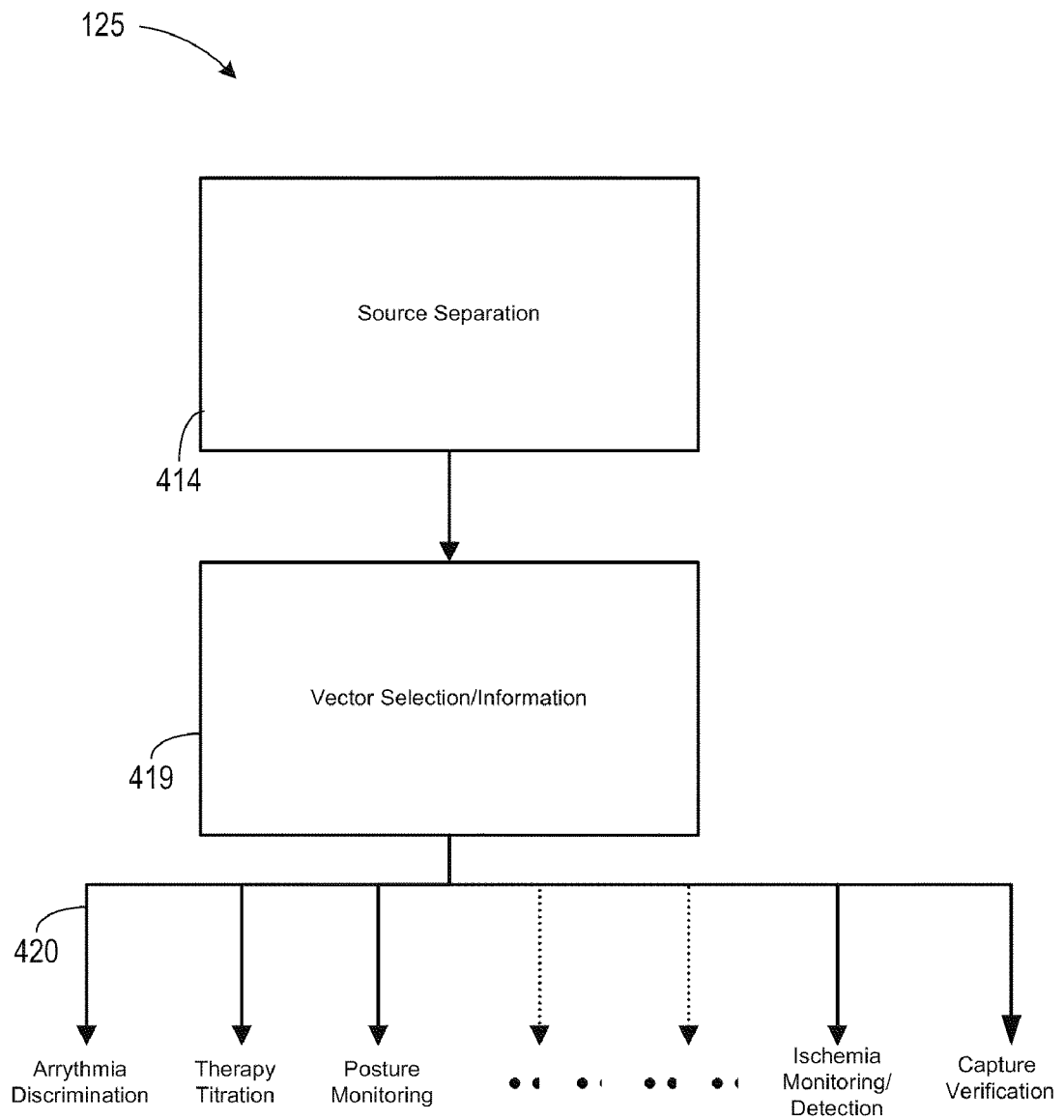
FIG. 10 is a block diagram illustrating uses of vector selection in accordance with the present invention.
Figure 11:
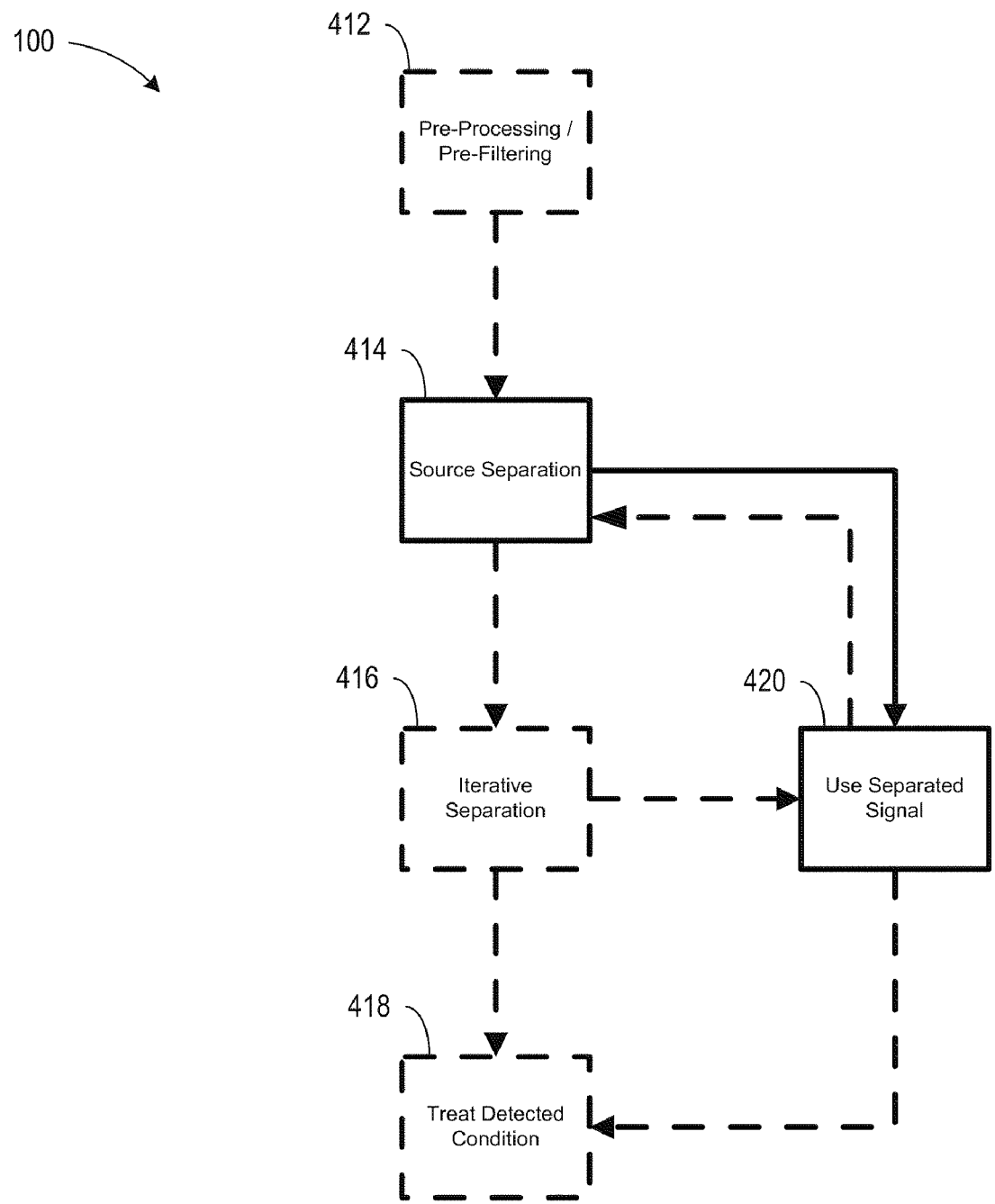
FIG. 11 is a block diagram of a signal separation process in accordance with the present invention.
Figure 12:
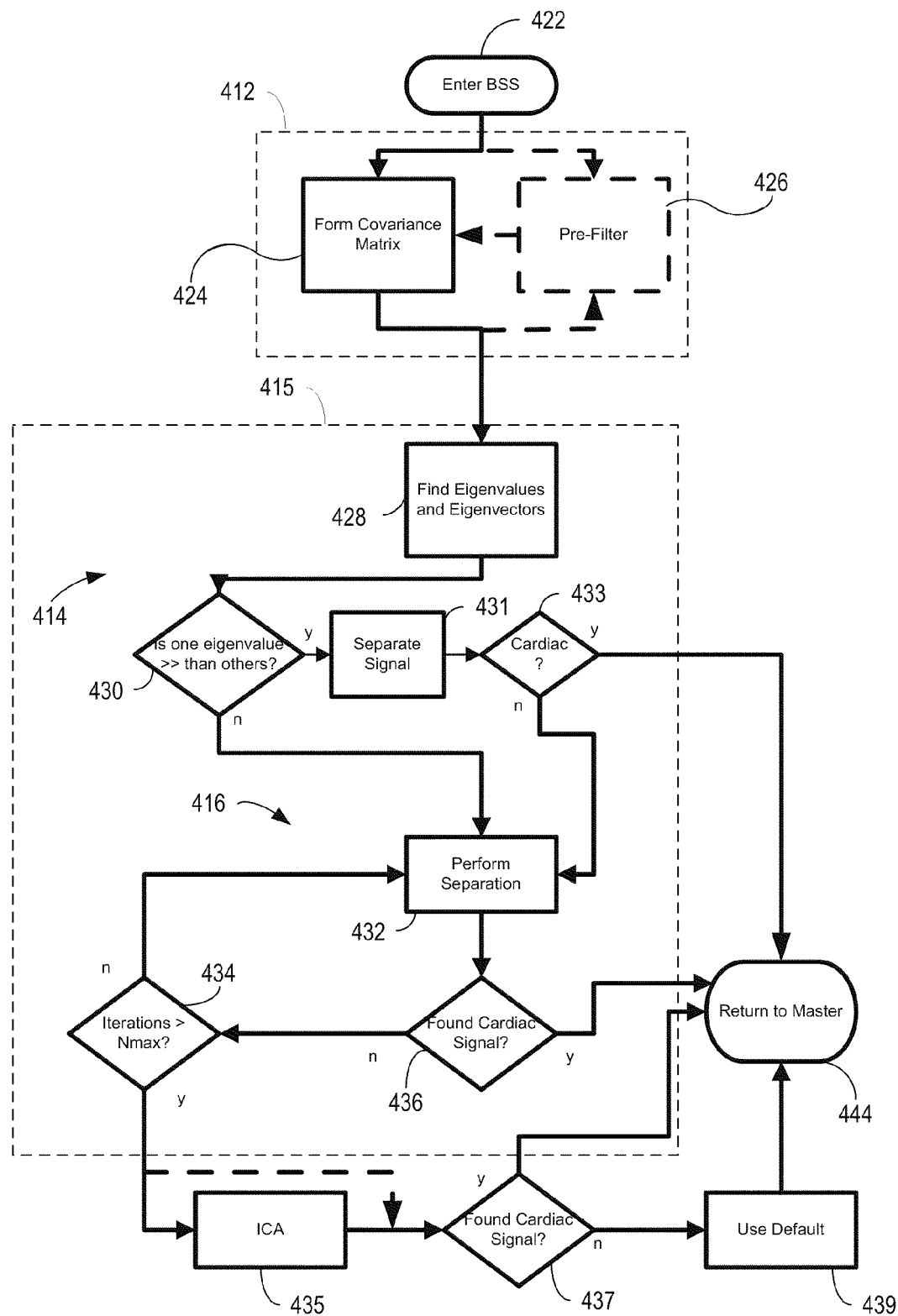
FIG. 12 is an expanded block diagram of the process illustrated in FIG. 11, illustrating an iterative independent component analysis in accordance with the present invention.

Referring now to FIGS. 10 through 12, cardiac sensing and/or stimulation devices and methods employing cardiac signal separation are described in accordance with the present invention. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise). The PIMD may be implemented to separate these components according to their sources and project the ECG signal in the direction along which the power of the cardiac signal is maximized or the signals are the most correlated. To achieve this, the methods and algorithms illustrated in FIGS. 10 through 12 may be implemented.

FIG. 10 illustrates a vector selection system 125 in accordance with the present invention. A vector selection process 414 is performed, providing a selected vector 419 along with vector selection information including, for example, magnitude, phase angle, rates of change, trend information, and other statistics. The selected vector 419 (and associated signal and other vector selection information) is available for a variety of uses 420, such as, for example, arrhythmia discrimination, therapy titration, posture detection/monitoring, ischemia detection/monitoring, capture verification, disease diagnosis and/or progress information, or other use. In accordance with the present invention, the vector selection process may be used, and repeated, to track changes in the progression of patient pathology, and to update sense vectors useful for cardiac sensing and/or stimulation.

FIG. 11 illustrates an embodiment of a signal source separation/update process 100 useful for vector selection in accordance with the present invention. A set of composite signals, including at least two and up to n signals, are selected for separation, where n is an integer. Each electrode provides a composite signal associated with an unknown number of sources. Pre-processing and/or pre-filtering 412 may be performed on each of the composite signals. It may be advantageous to filter each composite signal using the same filtering function. Source separation 414 is performed, providing at least one separated signal. If a treatment is desired, an appropriate treatment or therapy 418 is performed. If continued source separation is desired, the process returns to perform such source separation 414 and may iteratively separate 416 more signals until a desired signal is found, or all signals are separated.

The separated signal or signals may then be used 420 for some specified purpose, such as, for example, to confirm a normal sinus rhythm, determine a cardiac condition, define a noise signal, or other desired use. One use in accordance with the present invention is defining a vector useful for cardiac sensing. Electrode arrays and/or the use of multiple electrodes provide for many possible vectors useful for sensing cardiac activity.

Over the useful life of an implantable device, changes may occur in one or both of the patient and the implantable device. Certain changes may result in less than optimum sensing of cardiac activity. As an extreme example, consider the failure of an electrode element in an electrode array. Before the failure, the element may be the most beneficial for cardiac activity monitoring, but after the failure, the cardiac signal is lost. The separation/update process 100 would determine that the vector associated with the failed electrode is no longer the best vector to determine cardiac activity, and a next-best vector may be determined. The use 420 of the results of the separation/update process 100 may be for the implantable device to update its cardiac sense vector to the newly established optimum vector.

Updating the vector to search for the optimum sense vector may be performed periodically, without the need to detect a loss of cardiac signal. For example, a PIMD may regularly perform an update of the sense vector used for cardiac discrimination, to keep performance of the PIMD improved and/or optimized. Updating may be useful, for example, when pathology, therapy, posture, patient activity level, device orientation, device migration, exceeding an arrhythmia detection rate zone or threshold, or other system or patient change/event occurrence suggests a change in vector to separate the cardiac signal may be useful.

For example, in an APM environment such as described with reference to FIG. 9, a PIMD in accordance with the present invention may have a controller and communications circuitry that transmits its cardiac composite signals to a bedside signal processor when the patient is asleep. The signal processor may perform a blind source separation and analysis of the composite signals during the patient's sleep cycle. The signal processor may then determine the appropriate vector or vectors for the PIMD, and reprogram the PIMD before the patient awakes. The PIMD may then operate with the latest programming until the next update.

FIG. 12 illustrates further embodiments of a signal source separation process in greater detail, including some optional elements. Entry of the process at block 422 provides access to a pre-processing facility 412, illustrated here as including a covariance matrix computation block 424 and/or a pre-filtering block 426 such as, for example, a band-pass filtering block. The composite signals processed at pre-processing block 412 are provided to a signal source separation block 415, which may include functionality of the source separation block 414 and iterative source separation block 416 shown in FIG. 11.

The signal source separation block 415 includes a principal component analysis block 428, which produces an associated set of eigenvectors and eigenvalues using a covariance matrix or composite signals provided by pre-processing block 412. A determination 430 is made as to whether one eigenvalue is significantly larger than any others in the set, making the dimension associated with this eigenvalue a likely candidate for association with the direction along which the power of the signal is maximized. If such a candidate is identified at block 430, the candidate signal may immediately be separated 431 and a determination 433 made to confirm whether the candidate signal is a cardiac signal, before returning 444 to the master PIMD routine that called the signal source separation process.

If there is no clear candidate eigenvalue, or if the largest value eigenvalue did not provide a signal of interest, an iterative process may be used to separate 432 and search 436 for the signal of interest (e.g., cardiac signal). This process 432, 436, 434 may be repeated until such a signal is found, or no more signals are separable 434 as determined by exceeding a predefined number of iterations $N_{max}$ or some other termination criterion. An example of such a criterion is an eigenvalue considered at the current iteration being proportionately smaller than the largest eigenvalues by some predetermined amount.

If the iterations 434 are completed and a cardiac signal is not found at 436, then an Independent component analysis 435 may be attempted to further process the signals in an attempt to find the cardiac signal. If a cardiac signal is still not found at decision 437, after exhausting all possibilities, then a set of default settings 439 may be used, or an error routine may be initiated.

In another embodiment of the present invention, a method of signal separation involves sensing, at least in part implantably, two or more composite signals using three or more cardiac electrodes or electrode array elements. The method may further involve performing a source separation using the detected composite signals, the source separation producing two or more vectors. A first vector and a second vector may be selected from the set of vectors.

The use of the terms first and second vector are not intended to imply that the vectors are the first and second vectors separated from the composite signal, but that a first vector and a second vector are selected from among any vectors available for a given composite signal. First and second signals may be identified from the detected plurality of composite signals using the first and second vectors respectively. The method then involves selecting either the first vector or the second vector as a selected vector based on a selection criterion.

Selection criteria may include finding the optimum vector for cardiac signal identification, finding a vector that provides the largest magnitude cardiac signal, or finding another particular signal of interest. For example, the first vector may be selected and used for cardiac activity sensing, and the second vector may then be selected and used for skeletal muscle activity sensing. The skeletal muscle signal may then be used to further discriminate arrhythmias from noise such as is further described in commonly owned U.S. patent application Ser. No. 10/816,464 entitled "Subcutaneous Cardiac Stimulation System with Patient Activity Sensing," filed Apr. 1, 2004, which is hereby incorporated herein by reference.

With continued reference to FIGS. 10 through 12, one illustrative signal source separation methodology useful with the present invention is described below. Such an approach is particularly well suited for use in a PIMD system. It is to be understood that the example provided below is provided for non-limiting, illustrative purposes only. Moreover, it is understood that signal source separation within the context of the present invention need not be implemented using the specific processes described below, or each and every process described below.

A collected signal may be pre-filtered to suppress broadly incoherent noise and to generally optimize the signal-to-noise ratio (SNR). Any noise suppression in this step has the additional benefit of reducing the effective number of source signals that need to be separated. A Principal Component Analysis (PCA) may be performed on the collected and/or pre-filtered signal, producing a set of eigenvectors and associated eigenvalues describing the optimal linear combination, in a least-squares sense, of the recorded signals that makes the components coming from different sources orthogonal to one another. As an intermediate step to performing the PCA, an estimate of the spatial covariance matrix may be computed and averaged over a relatively short time interval (on the order of 2-3 beats) to enhance those components that are mutually correlated.

Each eigenvalue corresponds to the power of the signal projected along the direction of each associated eigenvector. The cardiac signal component is typically identified by one of the largest eigenvalues. Occasionally, PCA does not achieve a substantially sufficient level of source independence. In such a case, an Independent Component Analysis (ICA) may be performed to determine the actual source direction, either upon the PCA-transformed signal, or directly upon the collected signal. The ICA consists of a unitary transformation based on higher-order statistical analysis.

For example, separation of two mixed sources may be achieved by rotating the complex variable formed from the signals on an angle that aligns their probability distributions with basis vectors. In another approach, an algorithm based on minimization of mutual information between components, as well as other approaches generally known in the field of ICA, may be used to achieve reconstructed source independence.

A PIMD may, for example, employ a hierarchical decision-making procedure that initiates a blind source separation algorithm upon the detection of a condition under which the target vector may change. By way of example, a local peak density algorithm or a curvature-based significant point methodology may be used as a high-level detection routine. Other sensors/information available to the PIMD may also trigger the initiation of a blind source separation algorithm.

The PIMD may compute an estimate of the covariance matrix. It may be sufficient to compute the covariance matrix for only a short time. Computation of the eigenvalues and eigenvectors required for the PCA may also be performed adaptively through an efficient updating algorithm.

The cardiac signal can be identified among the few (e.g., two or three) largest separated signals. One of several known algorithms may be used as a selection criterion. For example, local peak density (LPD) or beat detection (BD) algorithms may be used. The LPD algorithm can be used to identify the cardiac signal by finding a signal that has an acceptable physiologic range of local peak densities by comparing the LPD to a predetermined range of peak densities known to be acceptable. The BD algorithm will find a signal that has a physiologic range of beat rate. In the case where two signals look similar, a morphology algorithm, such as a local rate of occurrence may be used for further discrimination and/or as a selection criterion. It may be beneficial to use the same algorithm at different levels of hierarchy: 1) initiation of blind source separation algorithm; 2) iterative identification of a cardiac signal.

Mathematical development of an example of blind source separation algorithm in accordance with the present invention is provided as follows. Assume there are m source signals $s_1(t), \ldots, s_m(t)$ that are detected inside of the body, comprising a desired cardiac signal and some other independent noise, which may, for example, include myopotential noise, electrocautery response, etc. These signals are recorded simultaneously from k sensing vectors derived from subcutaneous sensing electrodes, where k>m in a preferred approach. By definition, the signals are mixed together into the overall voltage gradient sensed across the electrode array. In addition, there is usually an additive noise attributable, for example, to environmental noise sources. The relationship between the source signals s(t) and recorded signals x(t) is described below:

$$\begin{pmatrix} x_1(t) \\ x_2(t) \\ \vdots \\ x_k(t) \end{pmatrix} = \begin{pmatrix} y_1(t) \\ y_2(t) \\ \vdots \\ y_k(t) \end{pmatrix} + \begin{pmatrix} n_1(t) \\ n_2(t) \\ \vdots \\ n_k(t) \end{pmatrix}$$

$$= \begin{pmatrix} a_{11} & a_{12} & \cdots & a_{1m} \\ a_{21} & a_{22} & \cdots & a_{2m} \\ \vdots & \vdots & \ddots & \vdots \\ a_{k1} & a_{k2} & \cdots & a_{km} \end{pmatrix} \begin{pmatrix} s_1(t) \\ s_2(t) \\ \vdots \\ s_m(t) \end{pmatrix} + \begin{pmatrix} n_1(t) \\ n_2(t) \\ \vdots \\ n_k(t) \end{pmatrix}$$

$$= x(t)$$
$$= y(t) + n(t)$$
$$= As(t) + n(t),$$

$$m < k$$

Here, x(t) is an instantaneous linear mixture of the source signals and additive noise, y(t) is the same linear mixture without the additive noise, n(t) is environmental noise modeled as Gaussian noise, A is an unknown mixing matrix, and s(t) are the unknown source signals considered here to comprise the desired cardiac signal and other biological artifacts. There is no assumption made about the underlying structure of the mixing matrix and the source signals, except for their spatial statistical independence. The objective is to reconstruct the source signals s(t) from the recorded signals x(t).

Reconstruction of the source signals s(t) from the recorded signals x(t) preferably involves pre-filtering x(t) to optimize the SNR (i.e., maximize the power of s(t) against that of n(t)). Here, a linear phase filter can be used to minimize time-domain dispersion (tails and ringing) and best preserve the underlying cardiac signal morphology. It is noted that the notation x(t) is substituted for the pre-filtered version of x(t).

An estimate of the spatial covariance matrix R is formed as shown immediately below. This step serves to enhance the components of the signal that are mutually correlated and downplays incoherent noise.

$$R = \frac{1}{T_{(\sim 1 \, sec)}} \sum_{t=1,T} \begin{pmatrix} x_1(t) \\ x_2(t) \\ \vdots \\ x_k(t) \end{pmatrix} * (x_1(t) \quad x_2(t) \quad \cdots \quad x_k(t))$$

$$= \frac{1}{T_{(\sim 1 \, sec)}} \sum_{t=1,T} \begin{bmatrix} x_1(t)*x_1(t) & x_1(t)*x_2(t) & \cdots & x_1(t)*x_k(t) \\ x_2(t)*x_1(t) & x_2(t)*x_2(t) & \cdots & x_2(t)*x_k(t) \\ \cdots & \cdots & \ddots & \cdots \\ x_k(t)*x_1(t) & x_k(t)*x_2(t) & \cdots & x_k(t)*x_k(t) \end{bmatrix}$$

Eigenvalues and eigenvectors of the covariance matrix R may be determined using singular value decomposition (SVD). By definition, the SVD factors R as a product of three matrices $R = USV^T$, where U and V are orthogonal matrices describing amplitude preserving rotations, and S is a diagonal matrix that has the squared eigenvalues $\sigma_1 \ldots \sigma_k$ on the diagonal in monotonically decreasing order. Expanded into elements, this SVD may be expressed as follows.

$$R = \begin{pmatrix} u_{11} & u_{12} & \cdots & u_{1k} \\ u_{21} & u_{22} & \cdots & u_{2k} \\ \vdots & \vdots & \ddots & \vdots \\ u_{k1} & u_{k2} & \cdots & u_{kk} \end{pmatrix} \begin{pmatrix} \sigma_1 & 0 & 0 & 0 \\ 0 & \sigma_2 & 0 & 0 \\ \vdots & \vdots & \ddots & \vdots \\ 0 & 0 & \cdots & \sigma_k \end{pmatrix} \begin{pmatrix} v_{11} & v_{12} & \cdots & v_{1k} \\ v_{21} & v_{22} & \cdots & v_{2k} \\ \vdots & \vdots & \ddots & \vdots \\ v_{k1} & v_{k2} & \cdots & v_{kk} \end{pmatrix}$$

The columns of matrix V consist of eigenvectors that span a new coordinate system wherein the components coming from different sources are orthogonal to one another. Eigenvalues $\sigma_1 \ldots \sigma_k$ correspond respectively to columns 1 ... k of V. Each eigenvalue defines the signal "power" along the direction of its corresponding eigenvector. The matrix V thus provides a rotational transformation of x(t) into a space where each separate component of x is optimally aligned, in a least-squares sense, with a basis vector of that space.

The largest eigenvalues correspond to the highest power components, which typically represent the mixed source signals $y_1(t), \ldots, y_m(t)$. The lower eigenvalues typically are associated with additive noise $n_1(t), \ldots, n_{k-m}(t)$. Each eigenvector may then be viewed as an optimal linear operator on x that maximizes the power of the corresponding independent signal component. As a result, the transformed signal is found as:

$$\hat{y}(t) = \begin{pmatrix} \hat{y}_1(t) \\ \vdots \\ \hat{y}_m(t) \end{pmatrix} = \begin{pmatrix} v_{11} & v_{21} & \cdots & v_{k1} \\ \vdots & \vdots & \ddots & \vdots \\ v_{1m} & v_{2m} & \cdots & v_{km} \end{pmatrix} * \begin{pmatrix} x_1(t) \\ x_2(t) \\ \vdots \\ x_k(t) \end{pmatrix}$$

The component estimates $\hat{y}_1(t), \ldots, \hat{y}_m(t)$ of $y_1(t), \ldots, y_m(t)$ are aligned with the new orthogonal system of coordinates defined by eigenvectors. As a result, they should be orthogonal to each other and thus independent.

In an alternative implementation, eigenvalues and eigenvectors of the covariance matrix R may be determined using eigenvalue decomposition (ED). By definition, the ED solves the matrix equation RV=SV so that S is a diagonal matrix having the eigenvalues $\sigma_1 \ldots \sigma_k$ on the diagonal, preferably in monotonically decreasing order, and so that matrix V contains the corresponding eigenvectors along its columns. The resulting eigenvalues and associated eigenvectors may be applied in similar manner to those resulting from the SVD of covariance matrix R.

In an alternative implementation, eigenvalues and eigenvectors are computed directly from x(t) by forming a rectangular matrix X of k sensor signals collected during a time segment of interest, and performing an SVD directly upon X. The matrix X and its decomposition may be expressed as follows.

$$X = \begin{pmatrix} x_1(t) \\ x_2(t) \\ \vdots \\ x_k(t) \end{pmatrix} = \begin{pmatrix} x_1(t_1) & x_1(t_2) & \cdots & x_1(t_T) \\ x_2(t_1) & x_2(t_2) & \cdots & x_2(t_T) \\ \vdots & \vdots & \ddots & \vdots \\ x_k(t_1) & x_k(t_2) & \cdots & x_k(t_T) \end{pmatrix} = USV^T$$

Note that in cases where T>k, a so-called "economy-size" SVD may be used to find the eigenvalues and eigenvectors efficiently. Such an SVD may be expressed as follows, expanded into elements.

$$X = USV^T$$

$$= \begin{pmatrix} u_{11} & u_{12} & \ldots & u_{1T} \\ u_{21} & u_{22} & \ldots & u_{2T} \\ \vdots & \vdots & \ddots & \vdots \\ u_{k1} & u_{k2} & \ldots & u_{kT} \end{pmatrix} \begin{pmatrix} \sigma_1 & 0 & \ldots & 0 \\ 0 & \sigma_2 & \ldots & 0 \\ \vdots & \vdots & \ddots & \vdots \\ 0 & 0 & \ldots & \sigma_k \end{pmatrix} \begin{pmatrix} v_{11} & v_{12} & \ldots & v_{1k} \\ v_{21} & v_{22} & \ldots & v_{2k} \\ \vdots & \vdots & \ddots & \vdots \\ v_{k1} & v_{k2} & \ldots & v_{kk} \end{pmatrix}$$

A similar economy-sized SVD may also be used for the less typical case where k>T. The matrices S and V resulting from performing the SVD of data matrix X may be applied in the context of this present invention identically as the matrices S and V resulting from performing the SVD on the covariance matrix R.

At this point, the mutual separation of $\hat{y}_1(t), \ldots, \hat{y}_m(t)$ would be completed, based on the covariance statistics. Occasionally, information from covariance is not sufficient to achieve source independence. This happens, for example, when the cardiac signal is corrupted with electrocautery, which may cause perturbations from the linearly additive noise model. In such a case, Independent Component Analysis (ICA) can be used to further separate the signals.

The ICA seeks to find a linear transformation matrix W that inverts the mixing matrix A in such manner as to recover an estimate of the source signals. The operation may be described as follows.

$$s(t) = \begin{pmatrix} s_1(t) \\ s_2(t) \\ \vdots \\ s_m(t) \end{pmatrix} = Wy(t) \approx A^{-1}y(t)$$

Here we substitute s(t) for the recovered estimate of the source signals. The signal vector y(t) corresponds to either the collected sensor signal vector x(t) or to the signal $\hat{y}(t)$ separated with PCA. The matrix W is the solution of an optimization problem that maximizes the independence between the components $s_1(t), \ldots, s_m(t)$ of s(t)=Wy(t). We treat the components of s(t) as a vector of random variables embodied in the vector notation s, so that the desired transformation would optimize some cost function $C(s)=C[s_1(t), \ldots, s_m(t)])$ that measures the mutual independence of these components. Given the joint probability density function (pdf) $f(s)$ and the factorized pdf $\bar{f}(s)=f_1(s_1)f_2(s_2)\ldots f_m(s_m)$, or given estimates of these pdf's, we may solve the following.

$$\min_W C(s) = \min_W \int D(f(s), \bar{f}(s))ds$$

The function $D(f(s), \bar{f}(s))$ may be understood as a standard distance measure generally known in the art, such as for example an absolute value difference $|f(s)-\bar{f}(s)|$, Euclidean distance $(f(s)-\bar{f}(s))^2$, or p-norm $(f(s)-\bar{f}(s))^p$. The distance measure approaches zero as $f(s)$ approaches $\bar{f}(s)$, which by the definition of statistical independence, occurs as the components of s approach mutual statistical independence.

In an alternative implementation, the distance measure may take the form of a Kullback-Liebler divergence (KLD) between $f(s)$ and $\bar{f}(s)$, yielding cost function optimizations in either of the following forms.

$$\min_W C(s) = \min_W \int f(s) \log \frac{f(s)}{\bar{f}(s)} ds \text{ or}$$

$$= \min_W \int \bar{f}(s) \log \frac{\bar{f}(s)}{f(s)} ds$$

Since the KLD is not symmetric, the two alternative measures are related but not precisely equal. One measure could be chosen, for example, if a particular underlying data distribution favors convergence with that measure.

Several alternative approaches may be used to measure the mutual independence of the components of s. These may include the maximum likelihood method, maximization of negentropy or its approximation, and minimization of mutual information.

In the maximum likelihood method, the desired matrix W is found as a solution of the following optimization problem, $$\max_W \sum_{j=1}^{T} \sum_{i=1}^{m} \log f_i(s_i(t_j)) + T \log|\det W| =$$

$$\max_W \sum_{j=1}^{T} \sum_{i=1}^{m} \log f_i(w_i^T y(t_j)) + T \log|\det W|$$

where $w_i$ are columns of the matrix W. In the negentropy method, the cost function is defined in terms of differences in entropy between s and a corresponding Gaussian random variable, resulting in the following optimization problem, $$\max_W \{H(s_{gauss}) - H(s)\} = \max_W \left\{ \begin{array}{l} -\int f(s_{gauss}) \log f(s_{gauss}) ds_{gauss} + \\ \int f(s) \log(s) ds \end{array} \right\}$$

where H(s) is the entropy of random vector s, and $s_{gauss}$ is a Gaussian random vector chosen to have a covariance matrix substantially the same as that of s.

In the minimization of mutual information method, the cost function is defined in terms of the difference between the entropy of s and the sum of the individual entropies of the components of s, resulting in the following optimization problem $$\min_W \left\{ -\sum_{i=1}^{m} \int f(s_i) \log f(s_i) ds_i + \int f(s) \log f(s) ds \right\}$$

All preceding cost function optimizations having an integral form may be implemented using summations by approximating the underlying pdf's with discrete pdf's, for example as the result of estimating the pdf using well-known histogram methods. We note that knowledge of the pdf, or even an estimate of the pdf, can be difficult to implement in practice due either to computational complexity, sparseness of available data, or both. These difficulties may be addressed using cost function optimization methods based upon kurtosis, a statistical parameter that does not require a pdf.

In an alternative method a measure of independence could be expressed via kurtosis, equivalent to the fourth-order statistic defined as the following for the $i^{th}$ component of s $$\mathrm{kurt}(s_i) = E\{s_i^4\} - 3(E\{s_i^2\})^2 \qquad 5$$

In this case W is found as a matrix that maximizes kurtosis of s=Wy over all the components of s (understanding y to be a vector of random variables corresponding to the components of y(t)). In all the previous examples of ICA optimization the solution W could be found via numerical methods such as steepest descent, Newton iteration, etc., well known and established in the art. These methods could prove numerically intensive to implement in practice, particularly if many estimates of statistics in s must be computed for every iteration in W.

Computational complexity can be addressed by several means. To begin, the ICA could be performed on the PCA-separated signal $\hat{y}(t)$ with the dimensionality reduced to only the first few (or in the simplest case, two) principal components. For situations where two principal components are not sufficient to separate the sources, the ICA could still be performed pairwise on two components at a time, substituting component pairs at each iteration of W (or group of iterations of W).

In one example, a simplified two-dimensional ICA may be performed on the PCA separated signals. In this case, a unitary transformation could be found as a Givens rotation matrix with rotation angle $\theta$, $$W(\theta) = \begin{pmatrix} \cos\theta & \sin\theta \\ -\sin\theta & \cos\theta \end{pmatrix}$$

where $s(t) = W(\theta)y(t)$. Here $W(\theta)$ maximizes the probability distribution of each component along the basis vectors, such that the following is satisfied.

$$\theta = \operatorname*{argmax}_{\theta} \sum_{t=1}^{T} \log f(s(t) \mid \theta)$$

This optimal rotation angle may be found by representing vectors y(t) and s(t)

$$\xi = e^{i4\theta} E(\rho^4 e^{i4\varphi'}) = e^{i4\theta} E[(s_1 + is_2)^4] = e^{i4\theta}(\kappa_{40}^s + \kappa_{04}^s)$$

as complex variables in the polar coordinate form $y = y_1 + iy_2 = \rho e^{i\varphi}$, $s = s_1 + is_2 = \rho e^{i\varphi'}$ and finding the relationships between their phase angles $\varphi, \varphi': \varphi = \varphi' + \theta$, where $\theta$ is the rotation that relates the vectors. Then, the angle $\theta$ may be found from the fourth order-statistic of a complex variable $\xi$, where $\kappa^s$ is kurtosis of the signal s(t).

By definition, source kurtosis is unknown, but may be found based on the fact that the amplitude of the source signal and mixed signals are the same.

As a result, $4\theta = \hat{\xi}\,\mathrm{sign}(\hat{\gamma})$ with $\gamma = E[\rho^4] - 8 = \kappa_{40}^s + \kappa_{04}^s$ and $\rho^2 = s_1^2 + s_2^2 = y_1^2 + y_2^2$ In summary, the rotation angle can be estimated as:

$$\theta = \frac{1}{4} \mathrm{angle}(\hat{\xi}\,\mathrm{sign}(\hat{\gamma}))$$

where $$\hat{\xi} = \frac{1}{T}\sum_{t=1,T} \rho_t^4 e^{i4\varphi(t)} = \frac{1}{T}\sum_{t=1,T} (y_1(t) + iy_2(t))^4,$$

$$\hat{\gamma} = \frac{1}{T}\sum_{t=1,T} \rho_t^4 - 8 = \frac{1}{T}\sum_{t=1,T} (y_1^2(t) + iy_2^2(t))^4 - 8$$

After the pre-processing step, the cardiac signal is normally the first or second most powerful signal. In addition, there is usually in practice only one source signal that is temporally white. In this case, rotation of the two-dimensional vector $y = y_1 + iy_2 = \rho e^{i\varphi}$ is all that is required. In the event that more than two signals need to be separated, the Independent Component Analysis process may be repeated in pairwise fashion over the m(m−1)/2 signal pairs until convergence is reached, usually taking about $(1+\sqrt{m})$ iterations.

A PIMD that implements the above-described processes may robustly separate the cardiac signal from a low SNR signal recorded from the implantable device. Such a PIMD robustly separates cardiac signals from noise to allow for improved sensing of cardiac rhythms and arrhythmias.

The system operates by finding a combination of the spatially collected low SNR signals that makes cardiac signal and noise orthogonal to each other (independent). This combination achieves relatively clean extraction of the cardiac signal even from negative SNR conditions.

A PIMD may operate in a batch mode or adaptively, allowing for on-line or off-line implementation. To save power, the system may include the option for a hierarchical decision-making routine that uses algorithms known in the art for identifying presence of arrhythmias or noise in the collected signal and initiating the methods of the present invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
a plurality of implantable electrodes configured for sensing a plurality of composite signals associated with an unknown number of sources, the plurality of implantable electrodes comprising at least three spatially separated implantable electrodes;
a housing configured for implantation in a patient;
a control circuitry provided in the housing;
a memory provided in the housing;
a processing circuitry provided in the housing and coupled to the memory, the processing circuitry configured to perform a source separation that separates signal components of the sensed plurality of composite signals according to their sources to produce a set of signal vectors, the processing circuitry configured to:
select, from the set of signal vectors, a target vector associated with a target signal, the target vector representative of a signal vector of the set of signal vectors associated with higher quality cardiac data relative to other signal vectors of the set of signal vectors;
detect a change in a predetermined condition or an event occurrence indicating that changing which signal vector of the set of signal vectors is selected as the target vector may be useful in sensing cardiac activity; and
update, in response to the change in the predetermined condition or event occurrence, selection of the target vector by performing a subsequent source separation on the detected plurality of composite signals and reselecting the same or a different signal vector associated with higher quality cardiac data relative to other signal vectors of the set of signal vectors as the target vector based on the subsequent source separation; and communications circuitry provided in the housing and configured to facilitate communication of information between the housing and a device external of the housing.

2. The system according to claim 1, wherein the at least three spatially separated implantable electrodes are provided at the housing.

3. The system according to claim 1, wherein the at least three spatially separated implantable electrodes comprise at least four electrodes, and wherein one of the at least four electrodes does not lie in the same plane as the other of the at least four electrodes.

4. The system according to claim 1, wherein at least one of the at least three spatially separated implantable electrodes is provided at the housing and at least two of the at least three spatially separated implantable electrodes are provided on a cardiac lead arrangement.

5. The system according to claim 1, wherein the processing circuitry is configured to perform blind source separation that separates signal components of the sensed plurality of composite signals according to their sources to produce the set of signal vectors.

6. The system according to claim 1, wherein the processing circuitry is configured to update selection of the target vector in response to at least one of a change in orientation of the housing and a change of a signal to noise ratio of the target signal associated with the target vector.

7. The system according to claim 1, wherein the processing circuitry is configured to update selection of the target vector in response to at least one of detection of a pathologic change, exceeding an arrhythmia detection rate zone or threshold, patient activity level, postural change, and a therapy change.

8. The system according to claim 1, wherein the processing circuitry is configured to:
detect the change in the predetermined condition or event occurrence using a local peak density algorithm, a curvature-based significant point algorithm, or physiologic sensor information; and
update selection of the target vector by performing the subsequent source separation in response to the detected change in the predetermined condition or event occurrence.

9. The system according to claim 1, wherein the processing circuitry is configured to:
perform a principal component analysis (PCA) on the sensed plurality of composite signals; and
determine if the principal component analysis achieves a sufficient level of source independence; and
perform an independent component analysis (ICA) on the sensed plurality of composite signals or on the PCA-transformed signals to determine the actual source direction if the principal component analysis does not achieve the sufficient level of source independence.

10. The system according to claim 1, wherein the system defines a subcutaneous, extrathoracic cardiac monitor devoid of a pacing pulse generator, a cardiovertor or a defibrillator.

11. The system according to claim 1, wherein the system defines a pacemaker, a cardiovertor, a defibrillator, or a cardiac resynchronizer.

12. A system, comprising:
a plurality of implantable electrodes configured for sensing a plurality of composite signals associated with an unknown number of sources, the plurality of implantable electrodes comprising at least three spatially separated implantable electrodes;
a housing configured for implantation in a patient;
control circuitry provided in the housing;
a memory;
processing circuitry coupled to the memory and configured to perform a source separation that separates signal components of the sensed plurality of composite signals according to their sources to produce a set of signal vectors, the processing circuitry configured to:
select, from the set of signal vectors, a target vector associated with a target signal, the target vector representative of a signal vector of the set of signal vectors associated with higher quality cardiac data relative to other signal vectors of the set of signal vectors;
detect a change in a predetermined condition or an event occurrence indicating that changing which signal vector of the set of signal vectors is selected as the target vector may be useful in sensing cardiac activity; and
update, in response to the change in the predetermined condition or event occurrence, selection of the target vector by performing a subsequent source separation on the detected plurality of composite signals and reselecting the same or a different signal vector associated with higher quality cardiac data relative to other signal vectors of the set of signal vectors as the target vector based on the subsequent source separation; and
communications circuitry provided in the housing and configured to facilitate communication of information between the housing and a device external of the housing.

13. The system according to claim 12, wherein:
the housing comprises a can, a header, and an antenna;
a first electrode of the at least three spatially separated implantable electrodes is provided at the can;
a second electrode of the at least three spatially separated implantable electrodes is provided at the header; and
a third electrode of the at least three spatially separated implantable electrodes is provided at the antenna.

14. The system according to claim 12, wherein:
the housing comprises at least two of a can, a header, and an antenna;
a first electrode of the at least three spatially separated implantable electrodes is provided at one of the can, the header, and the antenna; and
a second electrode of the at least three spatially separated implantable electrodes is provided at another of the can, the header, and the antenna.

15. The system according to claim 12, wherein the at least three spatially separated implantable electrodes comprise at least four electrodes, and wherein one of the at least four electrodes does not lie in the same plane as the other of the at least four electrodes.

16. The system according to claim 12, wherein at least one of the at least three spatially separated implantable electrodes is provided at the housing and at least two of the at least three spatially separated implantable electrodes are provided on a cardiac lead arrangement.

17. The system according to claim 12, wherein the processing circuitry is configured to perform blind source separation that separates signal components of the sensed plurality of composite signals according to their sources to produce the set of signal vectors.

18. The system according to claim 12, wherein the system defines a subcutaneous, extrathoracic cardiac monitor devoid of a pacing pulse generator, a cardiovertor or a defibrillator.

19. The system according to claim 12, wherein at least the source separation is performed by processing circuitry provided in a patient-external device or system.

20. The system according to claim 12, wherein at least the source separation is performed by processing circuitry provided in a network server system.

* * * * *